(12) United States Patent
Guzman et al.

(10) Patent No.: US 11,198,118 B2
(45) Date of Patent: Dec. 14, 2021

(54) INTEGRATED MODULAR UNIT CONTAINING ONE OR MORE ANALYTE CONCENTRATOR-MICROREACTOR DEVICES TO BE COUPLED TO A CARTRIDGE-CASSETTE AND METHODS OF OPERATION

(71) Applicant: PRINCETON BIOCHEMICALS, INC, Princeton, NJ (US)

(72) Inventors: Norberto Guzman, East Brunswick, NJ (US); Daniel E. Guzman, East Brunswick, NJ (US)

(73) Assignee: PRINCETON BIOCHEMICALS, INC., Princeton, NJ (US)

( * ) Notice: Subject to any disclaimer, the term of this patent is extended or adjusted under 35 U.S.C. 154(b) by 855 days.

(21) Appl. No.: 15/938,752

(22) Filed: Mar. 28, 2018

(65) Prior Publication Data
US 2018/0280972 A1 Oct. 4, 2018

Related U.S. Application Data

(60) Provisional application No. 62/478,137, filed on Mar. 29, 2017.

(51) Int. Cl.
*B01L 3/00* (2006.01)
*G01N 1/40* (2006.01)
(Continued)

(52) U.S. Cl.
CPC .......... *B01L 3/502707* (2013.01); *G01N 1/40* (2013.01); *G01N 1/405* (2013.01);
(Continued)

(58) Field of Classification Search
None
See application file for complete search history.

(56) References Cited

U.S. PATENT DOCUMENTS

| 5,045,172 A | 9/1991 | Guzman |
| 5,202,010 A | 4/1993 | Guzman |

(Continued)

OTHER PUBLICATIONS

Guzman et al.; An emerging micro-scale immuno-analytical diagnostic tool to see the unseen. Holding promise for precision medicine and P4 medicine. Journal of Chromatography B, 1021: 14-29 (2016). doi: 10.1016/j.jchromb.2015.11.026.
(Continued)

*Primary Examiner* — Brian R Gordon
(74) *Attorney, Agent, or Firm* — Porzio Bromberg & Newman P.C.

(57) ABSTRACT

The present invention relates to an immunoaffinity device for capturing, isolating and purifying one or more analytes of interest present at high or low concentration in simple or complex matrices. The device is designed as an integrated modular unit that includes one or more analyte concentrator-microreactor devices anchored into a T-shaped support box, which is built-in or connected to a interchangeable cartridge-cassette of a capillary electrophoresis or liquid chromatography apparatus for the isolation, enrichment, derivatization, separation and characterization of small molecules and polymeric macromolecules, primarily protein and peptide biomarkers. The integrated modular unit is also designed to perform metabolic or bioactivity studies.

21 Claims, 19 Drawing Sheets

(51) Int. Cl.
  *G01N 27/447* (2006.01)
  *G01N 33/543* (2006.01)
(52) U.S. Cl.
  CPC . *G01N 27/44743* (2013.01); *G01N 33/54326* (2013.01); *B01L 2200/026* (2013.01); *B01L 2200/028* (2013.01); *B01L 2300/0838* (2013.01); *B01L 2300/0861* (2013.01); *G01N 27/44704* (2013.01); *G01N 2001/4038* (2013.01)

(56) References Cited

U.S. PATENT DOCUMENTS

| | | | | |
|---|---|---|---|---|
| 5,240,577 | A * | 8/1993 | Jorgenson | B01D 15/08 204/453 |
| 5,358,613 | A * | 10/1994 | Schneider | G01N 27/44743 204/453 |
| 5,413,686 | A | 5/1995 | Klein et al. | |
| 5,593,564 | A * | 1/1997 | Templin | G01N 27/44717 204/451 |
| 5,646,048 | A * | 7/1997 | Templin | G01N 27/44743 204/601 |
| 5,741,639 | A | 4/1998 | Ensing et al. | |
| 5,800,692 | A | 9/1998 | Naylor et al. | |
| 6,406,604 | B1 * | 6/2002 | Guzman | G01N 27/44704 204/601 |
| 8,518,346 | B1 * | 8/2013 | Chirica | B01L 9/527 422/502 |
| 9,146,234 | B2 | 9/2015 | Guzman | |
| 9,482,602 | B2 | 11/2016 | Guzman | |
| 9,696,299 | B2 * | 7/2017 | Guzman | G01N 27/44743 |
| 2003/0027203 | A1 * | 2/2003 | Fields | G01N 1/405 435/6.15 |
| 2003/0223796 | A1 * | 12/2003 | Barth | B01L 3/0244 400/124.01 |
| 2004/0017981 | A1 * | 1/2004 | Jovanovich | B01L 3/563 385/68 |
| 2005/0250145 | A1 * | 11/2005 | Hirabayashi | G01N 35/1097 435/5 |
| 2006/0171852 | A1 * | 8/2006 | Renzi | B01J 19/0093 422/400 |
| 2007/0039866 | A1 * | 2/2007 | Schroeder | C12Q 1/6874 210/265 |
| 2007/0111329 | A1 | 5/2007 | Guzman | |
| 2007/0280855 | A1 * | 12/2007 | Matteo | B01L 9/527 422/606 |
| 2008/0023330 | A1 * | 1/2008 | Viovy | B01L 7/525 204/450 |
| 2008/0038152 | A1 * | 2/2008 | Van Pelt | G01N 30/7266 285/384 |
| 2008/0041724 | A1 * | 2/2008 | Ozawa | G01N 27/447 204/601 |
| 2008/0223722 | A1 * | 9/2008 | Guzman | G01N 27/44708 204/453 |
| 2011/0236273 | A1 * | 9/2011 | Claussen | G01N 1/405 422/187 |
| 2012/0103816 | A1 * | 5/2012 | Guzman | B01L 3/502 204/602 |
| 2012/0285832 | A1 * | 11/2012 | Guzman | B01L 3/502753 204/603 |
| 2014/0065658 | A1 * | 3/2014 | Bertholle | A61K 6/30 435/29 |
| 2014/0200164 | A1 * | 7/2014 | Makarewicz, Jr. | B01L 3/502784 506/12 |
| 2015/0093304 | A1 | 2/2015 | Guzman | |
| 2015/0192544 | A1 * | 7/2015 | Breadmore | G01N 27/453 204/550 |
| 2015/0238966 | A1 * | 8/2015 | Berndt | B01L 3/52 436/179 |
| 2016/0123925 | A1 | 5/2016 | Guzman | |
| 2016/0129443 | A1 * | 5/2016 | Tovar | B01L 3/0268 506/27 |
| 2017/0370878 | A1 * | 12/2017 | Stebniski | G01N 27/44721 |

OTHER PUBLICATIONS

Peng J., et al., Acta Pharmaceutica Sinica B, vol. 6, issue 6, pp. 540-551, 2016.
Bladergroen MR, van der Burgt Y.E.M., Journal of Analytical Methods in Chemistry, vol. 2015, 250131, doi 10.1155/2015/250131, 2015.
Tetala K.K., et al., Analytica Chimica Acta, vol. 906, pp. 7-21, 2016.
Stepanova S., Journal of Separation Science, vol. 39, issue 1, pp. 198-211, 2016.
Pagaduan J.V., et al., Analytical Bioanalytical Chemistry, vol. 407, issue 23, pp. 6911-6922, 2015.
Guihen E., Electrophoresis, vol. 35, issue 1, pp. 138-146, 2014.
Hjertén S., Chromatographic Reviews, vol. 9, issue 2, pp. 122147-143219, 1967.
Phillips T.M., et al., Methods in Molecular Biology, vol. 1466, pp. 121-136, 2016.
Gasilova N., Girault H.H., Bioanalysis, vol. 7, issue 9, pp. 1175-1190, 2015.
Culig Z, Recent Results in Cancer Research, vol. 202, pp. 141-147, 2014.
Guzman N.A., Phillips T.M., Electrophoresis, vol. 32, issue 13, pp. 1565-1578, 2011.
Guzman N.A., Phillips T.M., Analytical Chemistry, vol. 73, issue 3, pp. 61A-67A, 2005.
Phillips TM, Smith P., Biomedical Chromatography, vol. 17, pp. 182-187, 2003.
Dallas DC, Guerrero A, Parker EA, Robinson RC, Gan J, German JB, Barile D, Lebrilla CB, Proteomics, vol. 15, pp. 1026-1038, 2015.
Smith LM, Kelleher NL, Nature Methods, vol. 10, pp. 186-187, 2013; doi: 10.1038/nmeth.2369.
Nedelkov D, Proteomes, vol. 5,27 (2017); doi: 10.3390/proteomes5040027.
International Search Report, PCT/US2018/024997, dated Jun. 1, 2018.
Han M, Pearson JT, Wang Y, Winters D, Soto M, Rock DA, Rock BM Analytical Biochemistry, vol. 539, 1180126, 2017.
Nguyen LA, He H, Pham-Huy C, International Journal of Biomedical Science, vol. 2, pp. 85-100, 2006.
DeBerardinis RJ, Thompson CB, Cell, vol. 148, pp. 1132-1144, 2012; doi: 10.1016/j.cell.2012.02.032.
Michaelis S, Robelek R, Wegener J, Advances in Biochemical Engineering/Biotechnology, vol. 126, pp. 33-66, 2012; doi: 10.1007/10_2011_112.
Kim D, Herr AE, Biomicrofluidics, vol. 7, doi: 10.1063/1.4816934,1013.
Lu G, Crihfield CL, Gattu S, Veltri LM, Holland LA, Chemical Reviews in press, 2018.
Datta S, Christena LR, Rajaram YRS, 3 Biotech, vol. 3, pp. 1-9, 2012.

\* cited by examiner

INTEGRATED MODULAR UNIT CONTAINING ONE OR MORE ANALYTE CONCENTRATOR-MICROREACTOR DEVICES TO BE COUPLED TO A CARTRIDGE-CASSETTE AND METHODS OF OPERATION

BACKGROUND OF THE INVENTION

Field of the Invention

The field of the invention relates generally to the analysis of chemical and biological materials and, more particularly, to a modular, multi-task, immunoaffinity device secured to a cartridge-cassette which is connected to a capillary electrophoresis instrument for the isolation, enrichment, separation, identification and characterization of protein and peptide biomarkers and a large diversity of analytes found at a wide range of concentrations in simple and complex mixtures.

Description of Related Art

Given the complexity of most biological samples (e.g., serum, urine, saliva, tears, breath exhale, other bodily fluids, tissues, cells, vesicles), sample preparation has been, and continues to be, one of the critical challenges in bioanalysis, in particular biomarker discovery. Numerous techniques have been developed over the years to quantify small molecules and biomolecules. Demands for small volumes, shorter running times, reliability, robustness, selectivity, precision, versatility, accuracy, and sensitivity have been most challenging. Biomarker discovery practically includes tools and technologies that aid in the understanding of prediction, cause, diagnosis, regression and outcome of disease. Particularly, there have been efforts to transform biological analytical methods into more efficient and sensitive assays employing miniaturized analytical instruments coupled to powerful detectors, including laser-induced fluorescence and mass spectrometers. Solid-phase extraction and its different versions, specifically their applications in the development of selective and sensitive bioanalytical methods have been described (see Guzman N A, Guzman D E, Journal of Chromatography B, volume 1021, pages 14-29, 2016, doi: 10.1016/j.jchrom.2015.11.026, and references within; Peng J, Tang F, Zhou R, Xie X, Li S, Xie F, Yu P, Mu L. Acta Pharmaceutica Sinica B, volume 6, issue 6, pages 540-551, 2016, doi: 10. 10.1016/j.apsb.2016.05.016; Bladergroen M R, van der Burgt Y E M, Journal of Analytical Methods in Chemistry, volume 2015, 250131, 2015, doi: 10.1155/2015/250131).

Although most sample preparation methods have been designed to work with bulky conventional separation instruments, more recently sample preparation coupled to miniaturized instruments are becoming of interest to the scientific community. Miniaturized instruments and devices are ideally suited for using small volumes of samples and reagents, performing chemical and biochemical reactions in short periods of time, under controllable microenvironments, cost effective, environmental friendly and portables (see Tetala K K R, Vijayalakshmi M A, Analytica Chimica Acta, volume 906, pages 7-21, 2016, doi: 10.1016/j.aca.2015.11.037; Stepanova S, Kasicka V, Journal of Separation Science, volume 39, issue 1, pages 198-211, 2016, doi: 10.1002/jssc.201500973; Pagaduan J V, Sahore V, Wooley A T, Analytical Bioanalytical Chemistry, volume 407, issue 23, pages 6911-6922, 2015, doi: 10.1007/s00216-015-8622-5; Guihen E., Electrophoresis, volume 35, issue 1, pages 138-146, 2014, doi: 10.1002/elps.201300359).

As the power of fabrication allows the manufacturing of small devices with feature sizes as small as a few microns, it becomes inevitable that the requirement of sample volumes also becomes small. As a consequence, very small sample volumes compromises the issue of sensitivity making difficult the process of isolation and quantification of analytes of interest and/or their respective modified and/or altered corresponding counterpart found at low concentrations in complex matrices, in particular biological samples. Furthermore, there are a large amount of molecules and cellular structures in biological fluids, with an enormous variety in terms of type, shape, size and function, with a range of concentration that spans many orders of magnitude. Therefore, the use of miniaturized instrumentations and devices in the discovery of chemical, biochemical, cellular, subcellular and vesicular biomarkers present in biological fluids has encountered a number of challenges and faces many critical concerns.

One representative technology that utilizes small amounts of biological fluids for the determination of chemicals, biochemical, cellular, subcellular and vesicular compounds or entities is capillary electrophoresis, the technology can include capillary format or microchip format. Although capillary electrophoresis technology is reaching maturity, since Stellan Hjerten first introduced it in 1967 (Hjerten S. Chromatographic Reviews, volume 9, issue 2, pages 122-219, 1967), there are still technical issues to be resolved, in order to improve concentration sensitivity to monitor the separated analytes. In particular, when quantifying analytes present in simple and complex samples at concentrations below sub-nanomolar levels. Additionally, crucial to the importance of enhancing the sensitivity of the analytes, it is also important to isolate and purify each of the analytes of interest present in the mixture of simple and complex samples.

A conventional tool to isolate, purify and enrich target analytes, in particular proteins and peptides, is immunoaffinity chromatography and related techniques. An affinity ligand, usually an antibody, an antibody fragment, a lectin, or an aptamer are preferentially immobilized on a solid support. The binding of the affinity ligand must be carried out with an appropriate orientation to facilitate the optimal binding of the immobilized affinity ligand with a specific target analyte. The solid support can be made of glass or plastic, or any polymeric material and with a preferential architecture. Also, the solid support can be made of magnetic materials where affinity ligands can be immobilized, and magnetic beads or structures can be maintained in a stable and steady position and utilized with the help of one or more magnets. When affinity chromatography principles are applied to capillary electrophoresis, in conventional or microchip formats, the tool can be applied to many fields, including clinical laboratories, pharmaceutical industries, forensic laboratories, food and beverage industries, environmental science, military applications, cultural heritage (authenticity of art work), and research and development (see Phillips T M, Electrophoresis, volume 39, issue 1, pages 126-135, 2018, doi: 10.1002/elps.201700283; Guzman N A, Guzman D E, Journal of Chromatography B, volume 1021, pages 14-29, 2016, doi: 10.1016/j.jchrom.2015.11.026; Gasilova N, Girault H H, Bioanalysis, volume 7, issue 9, pages 1175-1190, 2015, doi: 0.4155/bio.15.49; Han M, Pearson J T, Wang Y, Winters D, Soto M, Rock D A, Rock B M Analytical Biochemistry, volume 539, 1180126, 2017, doi: 10.1016/j.ab.2017.10.005; 2013; Guzman N A, Phillips T M, Electrophoresis, volume 32, issue 13, pages 1565-1578, 2011, doi: 10.1002/elps.201000700; Guzman N A, Phillips T M, Analytical Chemistry, volume 73, issue 3, pages 61A-67A, 2005).

A series of solid-phase micro-extraction devices, based on affinity chromatography principles, have been described for selective and non-selective molecular consolidation. These devices, which are used on-line with a capillary tube or a micro-channel, are commonly known as analyte concentrators, containing affinity probes immobilized to a solid support or directly to the inner wall of the capillary tube or micro-channel, to bind target compounds. Typical embodiments are described in U.S. Pat. No. 5,202,010, which is incorporated by reference in this disclosure. Other relevant teachings are provided by U.S. Pat. No. 5,741,639, which discloses the use of molecular recognition elements; and U.S. Pat. No. 5,800,692, which discloses the use of a pre-separation membrane for concentrating a sample.

Even with the advent of analyte concentrators, there is still a need to improve the sensitivity levels for compounds that exist in sub-nanomolar quantities or even smaller concentrations. This deficit is particular acute in the clinical environment where early detection of a single molecule may be essential for the identification of a life-threatening disease.

The uses of chromophores that bind specific groups of a compound have been used to enhance detectability of tagged compounds, but not all compounds can bind a chromophore, and therefore, pre-concentration on-line is an excellent tool to improve sensitivity of a non-abundant compound present in simple or complex mixtures. The use of an analyte concentrator to concentrate a pre-tagged compound, or tagged the compound after pre-concentration, provides maximum detectability of a compound when using capillary electrophoresis (see Phillips T M, Smith P, Biomedical Chromatography, volume 17, issues 2-3, pages 182-187, 2003, doi: 10.1002/bmc.240; Guzman N A, Guzman D E, Journal of Chromatography B, volume 1021, pages 14-29, 2016, doi: 10.1016/j.jchrom.2015.11.026).

Known capillary electrophoresis instruments are also limited by low-throughput, i.e, the number of samples that can be analyzed in a specific period of time. In addition, low-throughput can also be interpreted as the number of target low-abundance compounds that can be analyzed in a single sample. In most cases, the sample has to be processed off-line to be able to isolate, purify, and concentrate one or more target compounds present in one sample. This protocol can be time consuming, expensive, and prone to lose a certain amount of the target compound during the process of isolation and concentration.

U.S. Pat. No. 5,045,172, which is incorporated by reference, described an automated, capillary-based system apparatus with increased analytical speed. The '172 patent represents a significant improvement over the prior art. However, throughput is still relatively low because the instrument uses only one capillary, which perform single sample analysis, and in most cases the target analyte is found at low concentrations.

U.S. Pat. No. 5,413,686 describes a multi-functional analyzer using an array of capillary tubes. The '686 patent focuses on samples having relatively high concentrations. There is no appreciation of the loadability and sensitivity necessary for analyzing compounds present in diluted samples, or compounds present at low concentrations in a variety of liquids or fluids.

U.S. Pat. No. 9,146,234 recognizes the need for a multi-functional biomarker analyzer using two or more capillaries. The '234 patent recognizes the need for more than one analyte concentrator-microreactor device associated with the separation capillaries. The apparatus described in the '234 patent includes (a) a transport passage, (b) plurality of separation passages, each of the separation passages having an overlapping portion that overlaps the transport passage, and (c) a different biomarker concentrator in each of the overlapping portions and which concentrates at least one different biomarker from a specimen from an animal or human being introduced into the transport passage.

Conventional commercially available analytical separation instruments, including capillary electrophoresis, having a single separation column or a single separation capillary for separation of a wide range of compounds with no on-line capabilities of sample preconcentration are known. Particularly, when referring to the preconcentration of proteins and peptides, with or without post-translational modifications. On-line preconcentration systems have proved to be most effective in improving the performance of instrumental analysis for many compounds found at sub-nanomolar concentrations in biological samples. Enhancement of sensitivity is desired for the detection and quantification of small molecules and biomolecules, and their corresponding metabolites or modified molecular entities, for increasing the precision and the speed of the analysis, and lowering the cost of analysis.

Based on these deficiencies, there exists a need for an electrophoresis instrument having a cartridge-cassette with a built-in analyte concentrator device that permits higher loadability, better detectability of constituent analytes, and capable to isolate, purify, and concentrate on-line one or more compounds present in a simple or complex biological mixture.

SUMMARY OF THE INVENTION

In one aspect of the invention, a sample including a number of analytes of interest is passed through a relatively large-bore transport capillary orthogonal to a small-bore separation capillary. A staggered-shaped analyte concentrator-microreactor device is positioned at the intersection of a transport capillary or passage and a separation capillary or passage. The staggered configuration of the analyte concentrator-microreactor device is a partial-rectangular design where the inlet port of the transport capillary or passage ends in a parallel position to the outlet port localized on the same side of the inlet port. The staggered configuration of the analyte concentrator-microreactor device is not like a zig-zag arrangement of the internal tubular area of the device.

The analyte concentrator-microreactor device is mounted on a T-shaped support. The T-shaped support can be part of a built-in box of a cartridge-cassette. Alternatively, the T-shaped support can be part of an interchangeable unit that can be replaced in-and-out of the cartridge-cassette providing convenience for the user. Alternatively, the analyte concentrator-microreactor device itself can also be an interchangeable unit that can be mounted on the built-in box of the cartridge-cassette.

The analyte concentrator-microreactor device can include a solid support containing one or a plurality of different affinity ligands to isolate, purify, and concentrate one or more target compounds of interest present in a simple or complex mixture. Alternatively, the analyte concentrator-microreactor device contains affinity ligands immobilized directly to an internal wall of an internal area of the analyte concentrator-microreactor device, or contains affinity ligands immobilized to molecular entities or materials which were previously immobilized directly to an internal wall of an internal area of the analyte concentrator-microreactor device.

In one embodiment, the analyte concentrator-microreactor, containing four entrance-exit ports, is connected to four microvalves, of which each valve is connected to one of the four ports. Each of the four microvalves can be operated manually or by an electronic circuitry. In order to introduce the sample, containing the analytes of interest, through the transport capillary or passage, the two micro-valves localized at the inlet and outlet ports of the analyte concentrator-microreactor device and connected by connectors to the separation capillary or passage are closed. The two micro-valves localized at the inlet and outlet ports of the analyte concentrator-microreactor and connected by connectors to the transport capillary or passage are open. The sample can be introduced through the transport capillary or passage manually or by the use of a miniaturized pump operated by an electronic circuitry.

After the sample has been passed through the analyte concentrator-microreactor device in an orthogonal manner, and after the analytes of interest are captured by the concentrator matrix, a cleaning buffer system is applied to the analyte concentrator-microreactor, and to the transport capillary or passage, to free the system of salts and other non-relevant components. The buffer system must be suitable for maintaining an optimized binding between the target analytes and the corresponding capturing agent. The buffer system should be able to maintain the integrity of the affinity ligand immobilized to a solid support within a main channel of the analyte concentrator-microreactor device, or directly to the inner wall of the analyte concentrator-microreactor device.

A major advantage of introducing the samples in an orthogonal manner through the transport capillary or passage is that the separation capillary or passage is maintained free of unwanted compounds present in the simple or complex matrix with the help of micro-valves. Accordingly, the separation capillary or passage can be re-used multiple times without altering significantly the performance of the separation capillary or passage.

Once the analytes of interest are bound to the affinity ligands immobilized to the matrix positioned within the elongated portion of the analyte concentrator-microreactor device, or directly to the inner wall or channel of the analyte concentrator-microreactor device, and the system is cleaned by the cleaning buffer, a switch in the operation of the micro-valves is activated. The two micro-valves localized at the inlet and outlet ports of the analyte concentrator-microreactor device and connected by connectors to the transport capillary or passage are closed. The two micro-valves localized at the inlet and outlet ports of the analyte concentrator-microreactor and connected by connectors to the separation capillary or passage are open.

A separation buffer preserving the binding and integrity of the immobilized affinity ligands is introduced from the inlet side of the separation capillary or passage all the way to the outlet side of the separation capillary or passage. At this stage the system is ready to release the bound analytes from the immobilized affinity ligands. This process of releasing the bound analytes is known as elution or desorption process and consists of introducing a small amount or plug of an elution buffer or solution from the inlet side of the separation capillary or passage. The plug of an elution buffer or solution is composed of a low pH buffer, high pH buffer, an analog competing for the binding, a chaotropic agent that disrupts hydrogen bonding between water molecules such as urea or guanidine, or a combination of them, including the presence of a detergent, a reducing agent or other chemical substances. The plug of an elution buffer or solution can also contains a chromophore for the simultaneously release and derivatization of the bound analytes of interest.

After the bound analytes of interest are released from the analyte concentrator-microreactor device by a plug of an elution buffer, initially pushed into the separation capillary or passage, from the inlet side of the separation capillary or passage, by a small mechanical pressure, the process of separation starts by electrophoresis (electromigration), electro-osmotic flow, mechanical pressure, or a combination of electro-osmotic flow and mechanical pressure. The protocol of separation is based on the nature of the sample, the mode of capillary electrophoresis to be used, and if the separation capillary is open-tubular containing simply a buffer or it is filled with a polymeric material. Released analytes from the analyte concentrator-microreactor device, which are being separated within the separation capillary, are monitored by a detector positioned at the outlet area of the separation capillary.

In another aspect of the present invention, a sample including a number of analytes of interest is passed through directly from the inlet port of the separation capillary or passage forming part of the cartridge-cassette itself. The sample is passed through a portion of the separation capillary or passage, located near the inlet side of the separation capillary or passage, acting in this case as a transport capillary or passage. However, the sample does not exit at the outlet of the separation capillary or passage of the cartridge-cassette, but rather is passed through an analyte concentrator-microreactor device having an internal tubular structure of a shifted T-shaped configuration, continuing through the exit portion of the transport capillary or passage, and exiting at the outlet side of the transport capillary or passage. The analyte concentrator-microreactor device contains affinity ligands immobilized to a solid-support matrix localized within the internal channel of the analyte concentrator-microreactor device, or directly to the internal wall of the internal area of the analyte concentrator-microreactor device. In this embodiment, there are only two valves needed to control sample introduction and washes. A first portion of the separation capillary or passage, near the inlet side of the separation capillary or passage, functioning as a transport capillary or passage, can be of a relatively large-bore transport capillary until it connects with the analyte concentrator-microreactor device. For example, an external diameter for the capillary ranging from 50 micrometers to 600 micrometers, and an internal diameter ranging from 20 micrometers to 400 micrometers can be used. A second portion of the separation capillary, until the end of the outlet side of the separation capillary, is of a small-bore separation capillary. For example, an external diameter for the capillary ranging about 50 to about 400 micrometers, and an internal diameter ranging from about 5 micrometers to about 200 micrometers can be used.

In another aspect of the invention, a sample including a number of analytes of interest is passed through a separation capillary or passage or used as a transport capillary or passage, the same way as described above. In this embodiment the analyte concentrator-microreactor device, having only two ports, inlet and outlet, can be coupled in an area near the inlet side of the separation capillary or passage used as a transport capillary or passage. Alternatively, the analyte concentrator-microreactor can be made and positioned within an internal portion of the separation capillary or passage used as a transport capillary or passage.

The affinity ligands can be immobilized to a solid-support matrix localized within the internal channel of the analyte concentrator-microreactor device or area, or directly to the internal wall of the internal area of the analyte concentrator-microreactor device, positioned on the inlet side of the separation-transport capillary or passage. In this case, the first device with a shifted T-shaped configuration only serves as a coupler-connector to facilitate the exit of the sample and washing buffers passing through the transport capillary or buffer to a waste container.

In an alternative embodiment, two analyte concentrator-microreactor devices or areas are used. One analyte concentrator-microreactor device is localized in the separation capillary or passage that is used as a transport capillary or passage, and another analyte concentrator-microreactor device, having as the internal tubular structure a shifted T-shaped configuration, is localized at the connection of the separation capillary or passage used as a transport capillary or passage as described above.

In one embodiment having two analyte concentrator-microreactors devices or areas, the affinity ligands can be immobilized to a solid-support matrix localized within the internal area of the analyte concentrator-microreactor devices or areas, or directly to the internal wall of the internal channel of the two analyte concentrator-microreactor devices or areas. The solid support matrix containing the immobilized affinity ligands, can be maintained in place using two constricted areas or frit structures, or maintained with one or two fixed or rotating magnets if the particles can be made magnetic. Otherwise, the affinity ligands can be immobilized directly into the internal surfaces or channels of the areas used as analyte concentrator-microreactors devices, or the affinity ligands can be immobilized to molecular entities or materials which were previously immobilized directly to internal surfaces or channels of the areas used as the analyte concentrator-microreactor device.

Accordingly, it is a general object of the present invention to provide an improved electrophoresis apparatus having a cartridge-cassette with a built-in analyte concentrator-microreactor device with various structural configurations or designs to facilitate the performance of the analysis of a sample.

It is another object of the present invention to provide an improved cartridge-cassette for an electrophoresis apparatus having greater operating efficiency, detectability, and throughput.

An additional object of the present invention is to provide a user-friendly, sample preparation step which is designed to isolate, purify and concentrate one or more compounds present in a simple or complex biological mixture, and to eliminate unwanted analytes present in the mixture that occupy binding sites and contaminate the inner walls of the separation capillaries or passages.

It is another object of the present invention to provide an electrophoresis apparatus capable to perform on-line chemical and/or biochemical reactions using a single ACM device functioning as a microreactor, in which biological activities and/or metabolic studies can be performed.

In pharmacology, biological activity or pharmacology activity describes the beneficial or adverse effect of a drug, analyte, or a given agent on living matter. Biological activity is generally dosage-dependent. When related to racemic pharmaceutical drugs, in which cellular entities will interact with each racemic drug differently, and metabolize each enantiomer by a separate pathway to generate different pharmacological activity. It has been found that one isomer may produce the desired therapeutic activities, while the other may be inactive or, in worst cases, produce undesired or toxic effects (Nguyen L A, He H, Pham-Huy C, International Journal of Biomedical Science, volume 2, pages 85-100, 2006).

Metabolism, or metabolic studies, is broadly defined as the sum of biochemical processes in living organisms that either produce or consume energy. Metabolism is the set of life-sustaining chemical transformation within the cells of organisms. Pathway of core metabolism can then be separated conveniently into three classes: those that synthesize simple molecules or polymerize them into more complex macromolecules (anabolism); those that degrade molecules to release energy (catabolism); and those that help to eliminate the toxic waste produced by the other classes (waste disposal) (See DeBerardinis R J, Thompson C B, Cell, volume 148, pages 1132-1144, 2012; doi: 10.1016/j.cell.2012.02.032).

When cells are isolated from the organism and transferred to an in vitro environment for biomedical or biotechnological purposes, they may lose their specific differentiation and functions due to the absence of the three-dimensional tissue architecture and important molecular clues. In order to maintain the cellular phenotype in vitro for research, medical approaches or biotechnology applications it is important to provide a biocompatible environment. Besides the chemical composition of the growth medium, it is the surface of the cell culture vessels that is critical for cell survival and fate. There is not an ideal surface that is well-suited for all kinds of cells and all kinds of scenarios. Cells do not interact directly with the surface of a man-made material, but a pre-adsorbed layers of extracellular biomolecules mostly from the extracellular matrix. Components of the extracellular matrix, in particular collagen, may facilitate a uniform anchorage of cells to surfaces and may also facilitate their growth for better functioning within a certain environment (See Michaelis S, Robelek R, Wegener J, Advances in Biochemical Engineering/Biotechnology, volume 126, pages 33-66, 2012; doi: 10.1007/10_2011_112).

It is still another object of the present invention to provide an electrophoresis apparatus capable to perform on-line chemical and/or biochemical reactions using a single ACM device, and in a second ACM device positioned in-tandem in the same capillary to perform preconcentration reactions.

It is yet another object of the present invention to provide an electrophoresis apparatus having enhanced loadability and sensitivity which is capable of analyzing samples present in a wide range of concentrations, including those found at low concentrations in diluted liquids or fluids with simple or complex matrices.

Another object of the present invention is to provide an electrophoresis apparatus, which uses more than one separation method to sequentially permit binding to, and elution from, an analyte concentrator to effect the separation of one or more analytes.

Protein and peptide biomarkers are critical for the early detection of disease, prognosis, and therapy monitoring. The Human Genome Project has revealed that the number of genes identified is in the order of 20,000, rather than the 100,000 genes estimated. This finding led to the recognition that much of the machinery afforded by conventional biological machinery is at the level of protein variations rather than due to a high number of distinct genes. Various molecular events create distinct protein molecules that modulate a wide variety of biological processes, from cell signaling to gene regulation and activation of protein complexes. Numerous names or terminologies have been described in the literature when referring to protein complexity. Some of these names are: protein forms, protein isoforms, protein species, and protein variants. More recently the term "proteoform" has been used to designate all the different molecular forms in which the protein product of a single gene can be found, including changes due to genetic variations, alternatively spliced RNA transcripts, co-translational modifications, and post-translational modifications (Smith L M, Kelleher N L, Nature Methods, volume 10, pages 186-187, 2013; doi: 10.1038/nmeth.2369).

Conventional mass spectrometry has been used in proteomic discovery efforts. Several examples of clinical significant proteoforms have been desribed, including transferrin (associated with chronic alcohol abuse and congenital disorders of glycosylation), transthyretin (associated with familial amyloidosis), hemoglobin (associated with hemoglobinopathies such as thalassemia and in the case of Hb1Ac for monitoring long term glycemic control), and many other proteoform biomarkers. Although mass spectrometry offers several advantages over other techniques, unfortunately, the cost and complexity of current mass spectrometry protein tests are factors impeding their use in routine testing for clinical diagnosis (Nedelkov D, Proteomes, volume 5, 27 (2017); doi: 10.3390/proteomes5040027). As a consequence, there is little incentive for developing expensive clinical protein-peptide tests for routine analysis requiring the use of mass spectrometry. One option to overcome this problem is the use of the three ACM devices system described here. These ACM devices can provide accurate protein-peptide diagnostic tests that can be readily analyzed and at a much cheaper cost. Currently, there is a need for point-of-care instruments, using hybrid technologies in miniaturized formats, which are aimed to a wider clinical adoption for the quantification and characterization of high-abundance and low-abundance protein-peptide biomarkers. These miniaturized point-of-care instruments are of benefits not only in urban areas but also in rural and remote areas across the world.

Additional objects of the present invention will be apparent to those skilled in the relevant art.

The invention will be more fully described by references to the following drawings.

DETAILED DESCRIPTION OF THE INVENTION

Figure 1:
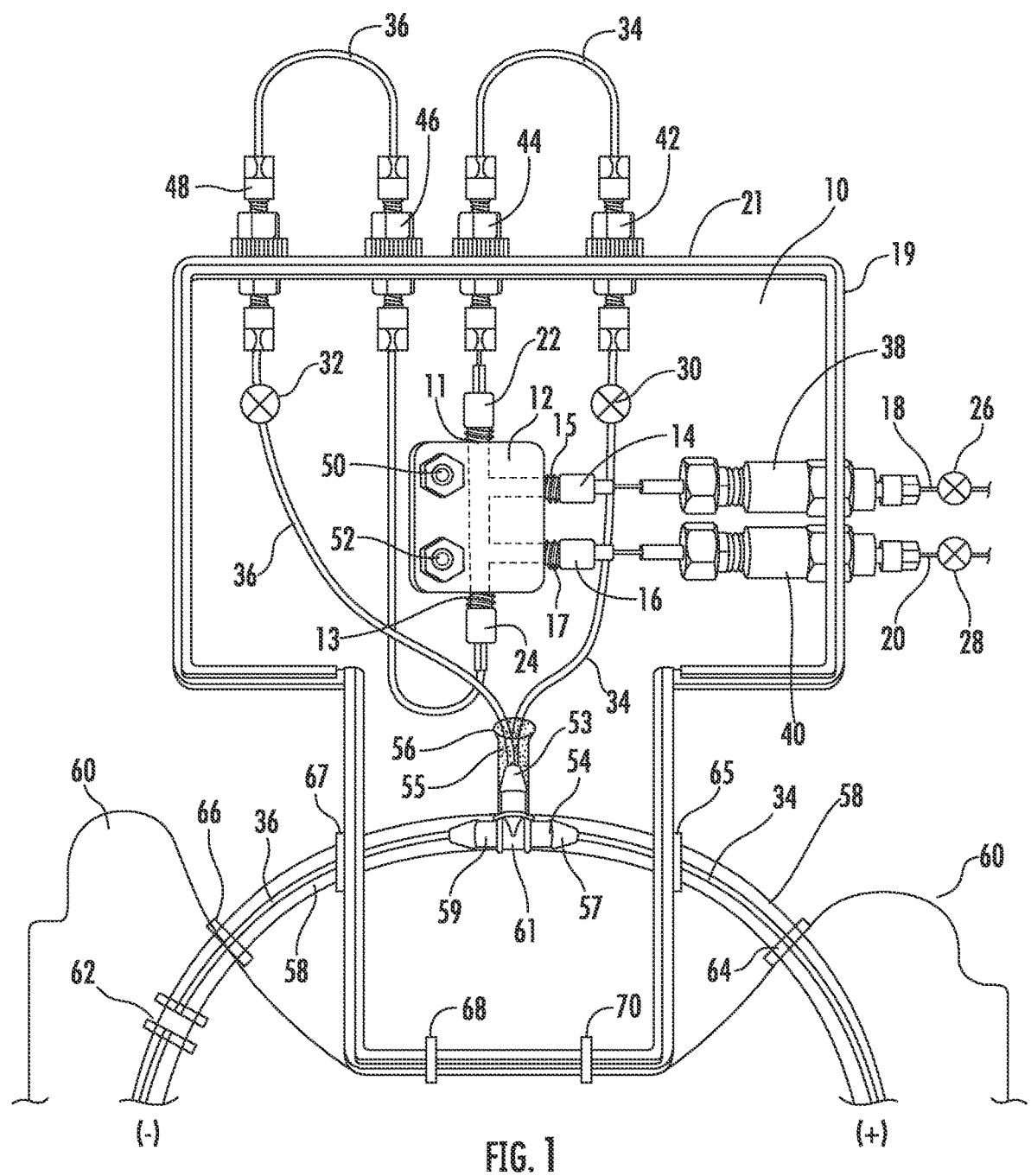
FIG. 1 is a perspective view of a T-shaped support embodiment of the present invention shown in an open configuration and containing an analyte concentrator-microreactor device connected to a cartridge-cassette of an electrophoresis apparatus.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 illustrates support box 10 of the present invention. Preferably, support box 10 can have a T-shaped support structure. Alternatively, support box 10 can have a rectangular or semi-circular shape. Support box 10 functions as a structural unit to provide anchoring of analyte concentrator-microreactor device 12. Support box 10 is attached to a cartridge-cassette unit 60 of an analytical separation apparatus. The analytical separation apparatus can be a capillary electrophoresis apparatus. Cartridge-cassette unit 60 includes a portion of a separation capillary or passage 34 which is connected to analyte concentrator-microreactor device 12 from inlet side 11 of separation capillary or passage 34 and a portion of separation capillary or passage 36 connected to analyte concentrator-microreactor device 12 from outlet side 13 of separation capillary or passage 36. Cartridge-cassette unit 60 also includes a portion of transport capillary or passage 18 which is connected to analyte concentrator-microreactor device 12 from inlet side 15 of transport capillary or passage 18 and a portion of transport capillary or passage 20 connected to analyte concentrator-microreactor 12 from outlet side 17 of transport capillary or passage 20. Integrated cartridge-cassette unit 60 including analyte concentrator-microreactor device 12 anchored to support box 10 and including the separation capillaries or passages 34 and 36 performs single sample studies on chemical and biochemical matrices having constituents or analytes of interest. Multiple affinity ligands can be immobilized to the matrix incorporated into one or more analyte concentrator-microreactor devices or directly to the inner walls or channels of one or more of these areas serving as analyte concentrator-microreactor devices, the integrated system can perform multiple analysis by capturing, purifying, detecting and measuring the presence of a plurality of analytes (for example, three). The affinity ligands can be of the same types (for example, three different antibodies for three different analytes of interest, or a combination of antibodies, lectins, or aptamers). Suitable and representative analytes can be proteins, peptides, pharmaceutical drugs, that may be present in urine, plasma, serum, sweat, exhaled breath, or other biological fluids, cell extracts, or vesicles, as well as other analytes of interest of small molecular mass or biomolecules having simple or complex structures. Analyte concentrator-microreactor 12 can function as a microreactor where one or more chemical or biochemical reactions can be performed. Suitable and representative reactions that be carried out in a microreactor are peptide synthesis, enzymatic reactions, and metabolic studies, when cells or sub-cellular entities can be encapsulated and maintained alive within the inner walls or channels of the one or more analyte concentrator-microreactor devices. The encapsulation of cellular receptors within the analyte concentrator-microreactor device 12 permits the performance of bioactivity studies.

As shown in FIG. 1, support box 10 houses analyte concentrator-microreactor device 12 having four entrance-exit ports, of which two ports serve as the places for connecting the transport capillary or passage 18 or transport capillary or passage 20 through respective connectors 14 and 16, and two ports serve as the places for connecting separation capillary or passages 34 or 36 through respective connectors 22 and 24. Connector 14 corresponds to an inlet area of the analyte concentrator-microreactor device 12 connecting to transport capillary or passage 18, where the sample under investigation, containing the analytes of interest, is introduced into the system via an inlet side of transport capillary or passage 18, connected to connector 38. Connector 16 corresponds to an outlet area of analyte concentrator-microreactor device 12 connecting to an outlet side of transport capillary or passage 20, using connector 40, where the sample under investigation has already passed analyte concentrator-microreactor device 12, and where the one or more analytes of interest have been captured and retained by one or more affinity ligands immobilized to the matrix or walls of the inner channel of analyte concentrator-microreactor device 12. Preferably, connector 38 and connector 40 are connected to side 19 of support box 10 to localize inlet side 15 of transport capillary or passage 18 and outlet side 17 of transport capillary of passage 20 on the same side of support box 10.

Analyte concentrator-microreactor device 12 is maintained anchored to support box 10 by screws 50 and 52. The flow of liquid passing through transport capillaries or passages 18 and 20, and separation capillaries or passages 34 and 36 is controlled by four micro-valves 26, 28, 30 and 32. When the sample under study containing one or more compounds, analytes or biomarkers of interest is passed from the inlet side of the transport capillary or passage 18 all the way to the exit side of the transport capillary or passage 20, micro-valves 26 and 28 are open and micro-valves 30 and 32 are closed. After the sample is passed through the matrix of analyte concentrator-microreactor device 12, where the analytes of interest will be captured and retained, an appropriate cleaning buffer solution is passed through the same path to remove all unwanted compounds of the sample under investigation that did not bind to the one or more affinity ligands immobilized to the surface of the matrix or walls or inner side of the channels. Once the tubular path system is clean, the micro-valves are switched in operation. Micro-valves 26 and 28 are closed, and micro-valves 30 and 32 are open.

A process of elution or release of the bound analytes from the corresponding affinity ligands immobilized to the matrix or surface of the inner wall or channel of the analyte concentrator-microreactor 12 is performed. The released analytes are further separated in a separation capillary or passage 34 or 36 and further detected by one or more detectors for quantification and characterization.

In a typical configuration, analyte concentrator-microreactor device 12 comprises a matrix-like assembly of the type shown in U.S. Pat. No. 5,202,010. The collective mass of the matrix is provided by large quantities of microstructures such as beads, platelets, chips, fibers, filaments, membranes or the like. Individual substrates can be made from glass, plastic, sol-gels, monolithic polymers or other polymeric material, ceramic, or metallic compositions, and mixtures thereof. Coated or otherwise properly oriented immobilized analyte-specific antibodies or other affinity chemistries, including lectins or aptamers, or a combination of them, which are suitable for the capture, purification, separation, quantification and characterization of particular analytes of interest. Representative antibodies include natural antibodies or laboratory-made monoclonal antibodies, mammal or avian or other vertebrate polyclonal antibodies, fragments of antibodies, single domain antibodies or camelid antibodies, or synthetic antibodies generated in vitro using an imprinting approach.

The present invention provides a user-friendly, sample preparation step, which is designated to capture, isolate and enrich one or more analytes of interest and to eliminate unwanted analytes that occupy binding sites and contaminate the inner walls of capillaries and channels. The isolation and enrichment step is accomplished by the use of analyte concentrator device 12, which connected to transport capillaries or passages 18 and 20 and separation capillaries or passages (34 and 36) capillaries, and integrated to cartridge-cassette unit 60 generates a powerful tool to separate, quantify and characterize target analytes or biomarkers found at a wide range of concentrations in simple and complex matrices.

In a first step, micro-valves 26 and 28 are placed in an open position and micro-valves 30 and 32 are placed in a closed position and a quantity of sample solution, of simple or complex composition, is introduced from an inlet of transport capillary or passage 18, passing through analyte concentrator-microreactor device 12, and exiting through transport capillary or passage 20 to a waste container (not shown). Sample introduction is carried out manually or using syringe pumps, by syringes capable of deliver volumes ranging from microliter volumes to several milliliter volumes, or the process can be automated controlled by an electronic circuitry delivering the wide range of volumes mechanically. Thereafter, a quantity of cleaning buffer is introduced into transport capillary or passage 18 in the same way as described for sample introduction. All unwanted compounds bound non-specifically to the inner surface of transport capillaries or passages 18 and 20 or even to certain areas of the matrix or inner wall of analyte concentrator-microreactor device 12 are removed during the cleaning process.

In a second step, micro-valves 26 and 28 are placed in a closed position and micro-valves 30 and 32 are placed in an open position and a quantity of separation buffer is introduced from a buffer vial (not shown) localized on the inlet side of separation capillary or passage 34, positioned at the inlet side of the base of cartridge-cassette unit 60, passing through analyte concentrator-microreactor device 12, and exiting in outlet side of separation capillary or passage 36 to a receiving vial or waste container (not shown), positioned at outlet side 69 of the base of cartridge-cassette unit 60. The separation buffer must be a suitable buffer capable of preserving the integrity of the immobilized affinity ligand, and for maintaining under optimal conditions the binding of the captured analyte of interest and the complementary affinity ligand immobilized to the matrix or inner surface of the elongated section of analyte concentrator-microreactor device 12. The separation buffer is usually introduced into separation capillary or passage 34 under pressure controlled by an electronic circuitry, part of the controlling system of the capillary electrophoresis instrument. Two vials or containers filled with separation buffer are placed on the base of the cartridge-cassette unit 60, one vial is positioned on the inlet side of the base and another vial is positioned on the outlet side of the base to make a closed operating system, comprising separation capillary or passage 34 connected to analyte concentrator-microreactor device 12, which in turn is connected to separation capillary or passage 36. Micro-valves 18 and 20 continue to be closed, and micro-valves 30 and 32 continue to be open.

Once the separation buffer is in place, filling the entire separation capillaries or passages 34 and 36, and analyte concentrator-microreactor device 12, a process of elution or release of the bound analytes of interest from analyte concentrator-microreactor 12 is performed. A small volume or plug of elution buffer or solution is introduced preferentially by a small pressure, but also can be introduced by electro-osmotic flow. The plug of an elution buffer or solution is composed of a low pH buffer, high pH buffer, an analog competing for the binding, a chaotropic agent that disrupt hydrogen bonding between water molecules such as urea or guanidine, changing the temperature (thermal elution), or a combination of them, including the presence of a detergent, a reducing agent or other chemical substances. The plug of an elution buffer or solution can also contain a chromophore for the simultaneously release and derivatization of the bound analytes of interest. Conceptually, the process of selective binding and release is simple. One or more affinity ligands are attached to a solid support to form a specific adsorbent to which the biological system, usually in the form of a homogenate or extract containing the molecular species of interest, are exposed. Only the molecular species that shows appreciable affinity for the ligands will be retained or retarded; other materials which have no specificity for the insolubilized ligand will pass through the column. The molecular species that has become attached to the adsorbent must then be eluted or released without destroying its biological properties. Optimal binding conditions typically occurs under physiological conditions, and an elution or desorption process occurs by temporarily lowering the effective strength of affinity binding to the target analyte. The process of elution must be fast. The need for fast but reversible binding and regeneration of the immobilized affinity ligand is especially important when an affinity column is to be used for a large number of samples. Usually the elution process is carried out in a single step. Alternatively, if more than one target analyte is bound to the affinity ligands immobilized to the matrix, and at different affinity binding strengths, then it is desirable to perform a sequential elution, meaning more than once and with changing in the constitution and pH of the elution buffer.

Thereafter the introduction of a plug of an elution buffer, a process of separation is performed in the separation capillary or channel, electrically, by electro-osmotic flow, mechanical pressure, or a combination of electro-osmotic flow and mechanical pressure. In open tubular capillary when the capillary is filled with buffer, the preferential method of separation is electro-osmotic flow or a combination of electro-osmotic flow and mechanical pressure. When the separation capillary is filled with a polymeric material, such as monolithic solid phase or sol-gels or similar solid phases, the preferential method of separation is by electrical charge. Mechanical pressure, such is the case of capillary high-pressure chromatography, is the method of choice for separation when the capillary is filled with a solid support made of glass or plastic beads, or a polymeric material.

As the plug of elution buffer or solution keep advancing within the separation capillary, starting from separation capillary or passage 34 positioned at inlet side 63 of the cartridge-cassette unit 60, and ending in separation capillary or passage 36 positioned at outlet side 69 of cartridge-cassette unit 60, it will pass through the elongated portion of analyte concentrator-microreactor device 12 releasing all analytes of interested bound to one or more affinity ligands immobilized to the matrix or inner wall or channel of analyte concentrator device 12. Detection of one or more released analytes of interest occurs at detection point 62 positioned at the outlet side of the separation capillary or passage 36 on outlet side 69 of cartridge-cassette unit 60. One or more on-line and/or off-line detectors can be positioned at detection point 62 at the outlet side of the separation capillary or passage 36, including ultraviolet, fluorescence, laser-induced fluorescence, chemiluminescence, bioluminescence, radiometry, conductivity, electrochemical, nuclear magnetic resonance, mass spectrometer, circular dichroism, Raman-infrared detection, and/or modified versions of these detectors. Detection can be made at a single point of separation capillary or passage 36, making a small detection area by removing a small portion of external coating material of the separation capillary or passage 36, such as polyimide. Detection can also be made in an extended area of the capillary or passage 36 by removing a larger portion of the external coating polymeric material polyimide. In this case to facilitate detection, a charge-coupled device (CCD) camera or image sensors can be used. Charge-coupled device is a silicon based multichannel array detector of ultraviolet, visible and near-infra light. The results obtained by one or more detectors can be further processed by a data acquisition system (not shown).

In order to maintain a steady temperature within separation capillaries or passages 34 and 36 an appropriation temperature control system is provided. The temperature control system can include an air ventilation system or a liquid temperature control system. The air ventilation system can be of various configurations, preferentially using some micro-fans or Peltier heat pumps (not shown) providing a desired temperature. The liquid temperature-control system can comprise tube 58 harboring within the separation capillaries or passages 34 and 36. Tube 58 can be a solid temperature-resistant tube. For example, tube 58 can be formed of plastic. A cooling-heating liquid can be passed through tube 58 for providing a desired temperature controlled by electronic circuitry. Tube 58 can have various shapes in order to be used as a temperature protector. The cooling-heating liquid passing through tube 58 must be kept within an enclosure that is sealed completely. In the present invention, tube 58 is connected to T-shaped connector 54 that allows separation capillary or passage 34 and separation capillary or passage 36 to converge into a connection-separation point. T-shaped connector 54 is formed of first arm 53, second arm 57 and third arm 59 which converge at connection-separation point 61. Separation capillary or passage 34 and separation capillary or passage 36 are both received in first arm 53 of T-shaped connector 54. Separation capillary or passage 34 extends through second arm 57 of T-shaped connector 54. Separation capillary or passage 36 extends through second arm 57 of T-shaped connector 54. T-shaped connector 54 is further connected to tubing 56 with the purpose of sealing the connecting point of separation capillaries or passages 34 and 36 with a sealing material and thus avoiding escape of cooling-heating fluid passing through an inner part of tube 58. Tubing 56 can be formed of plastic. Tube 58 is kept in a firm and steady position to cartridge-cassette unit 60 using connectors 64, 65, 66 and 67.

Support box 10 can be provided with two cooling-heating systems if necessary to maintain a uniform temperature within the concentration-separation system. One located at the bottom side of support box 10 and described above, which is the cooling-heating system facilitated by a liquid passing through tube 58. Another cooling-heating system located at the upper side of support box 10 (not shown) composed of micro-fans or a Peltier heat pump system.

T-shaped support box 10 is also kept in a stable and steady position connected to the cartridge-cassette unit 60 by screws 68 and 70. In order to maintain the entire concentration-separation system hermetically sealed and stable, separation capillaries or passages 34 and 36 are connected are various points by connectors coupled to support box 10. For transport capillaries or passages 18 and 20, connectors 38, 40, 14 and 16 are used. For separation capillaries or passages 34 and 36, connectors 22, 24, 42, 44, 46 and 48 are used.

Preferably, connector 44 and connector 46 are connected to upper side 21 of support box 10 to localize inlet side 11 of separation capillary or passage 34 and outlet side 13 of separation capillary of passage 36 on upper side 21 of support box 10. Similarly, on upper side 21 of support box 10 are located connectors 42 and 48.

Once the entire process of separation and data acquisition is finished, transport capillaries or passages 18 and 20 and separation capillaries or passages 34 and 36 are cleaned by a cleaning solution followed by an optimization buffer, preparing transport capillaries or passages 18 and 20 and separation capillaries or passages 34 and 36 for a new cycle of operation.

Figure 2:
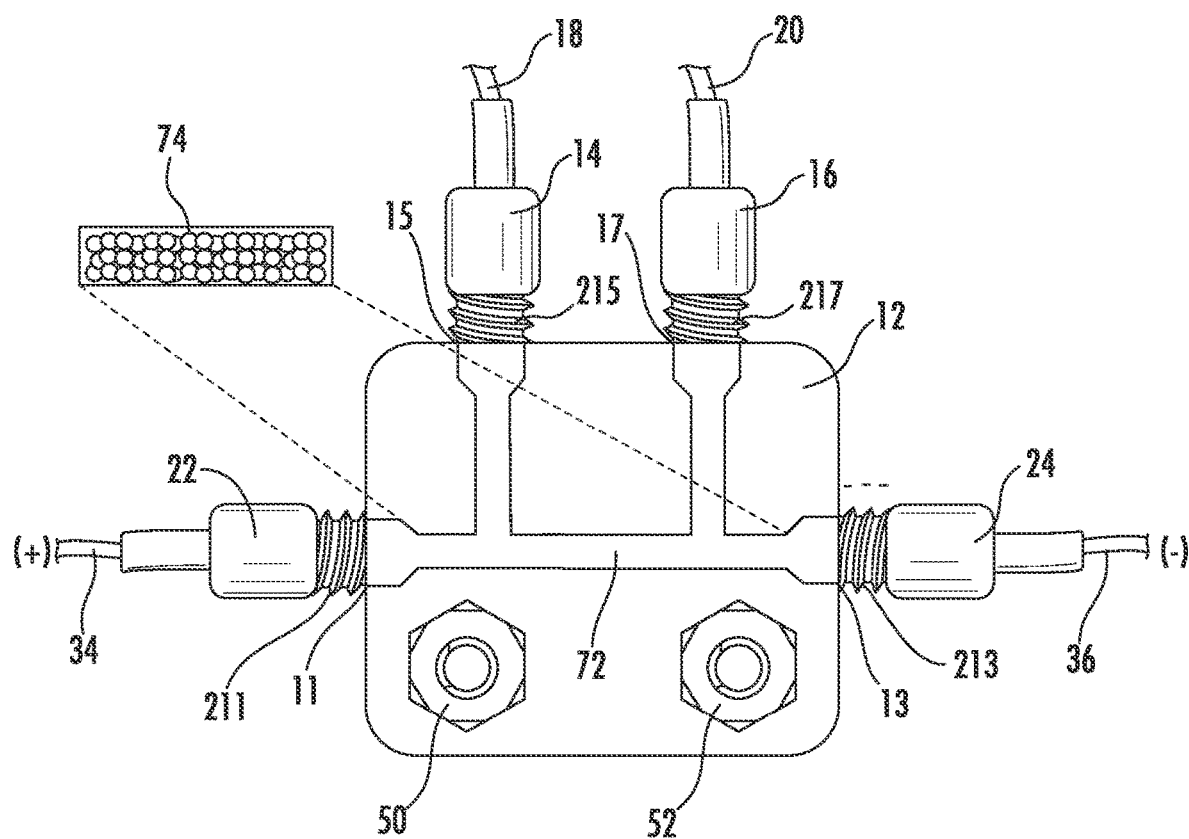
FIG. 2 is an enlarged elevation view of an analyte concentrator-microreactor device shown in FIG. 1.

FIG. 2 illustrates analyte concentrator-microreactor device 12 of the present invention. Analyte concentrator-microreactor device 12 functions as a structural unit composed of four entrance-exit ports where capture, concentration or microreactions occurs. Port 211 of analyte concentrator-microreactor device 12 is located at inlet side 11 of separation capillary or passage 34 and is the inlet side connection to a portion of separation capillary or passage 34 using connector 22. Port 213 of analyte concentrator-microreactor device 12 is located at outlet side 13 of separation capillary or passage 36 and is the outlet side connection to a portion of the separation capillary or passage 36 using connector 24. Between port 211 and port 213 there is an elongated tubular portion or channel 72 serving as the primary place where microstructures or polymeric materials 74 are deposited for the immobilization of affinity ligands. Elongated tubular portion or channel 72 is where the capture, isolation, purification, and enrichment of analytes of interest occur. Elongated tubular portion or channel 72 can also be used for immobilizing enzymes for microreactions to occur, or placing or encapsulating cells, subcellular structures, or cellular receptors to carry out metabolic studies and bioactivity studies. Port 215 of analyte concentrator-microreactor device 12 located at inlet side 15 of transport capillary or passage 18 is the inlet side connection to a portion of the transport capillary or passage 18 using connector 14. Port 217 of analyte concentrator-microreactor device 12 located at outlet side 17 of transport capillary or passage 20 is the outlet side connection to a portion of the transport capillary or passage 20 using connector 16. Preferably, port 215 and port 217 are positioned on the same side of analyte concentrator-microreactor device 12.

Analyte concentrator-microreactor device 12 is maintained anchored to support box 10 by screws 50 and 52.

Figure 3:
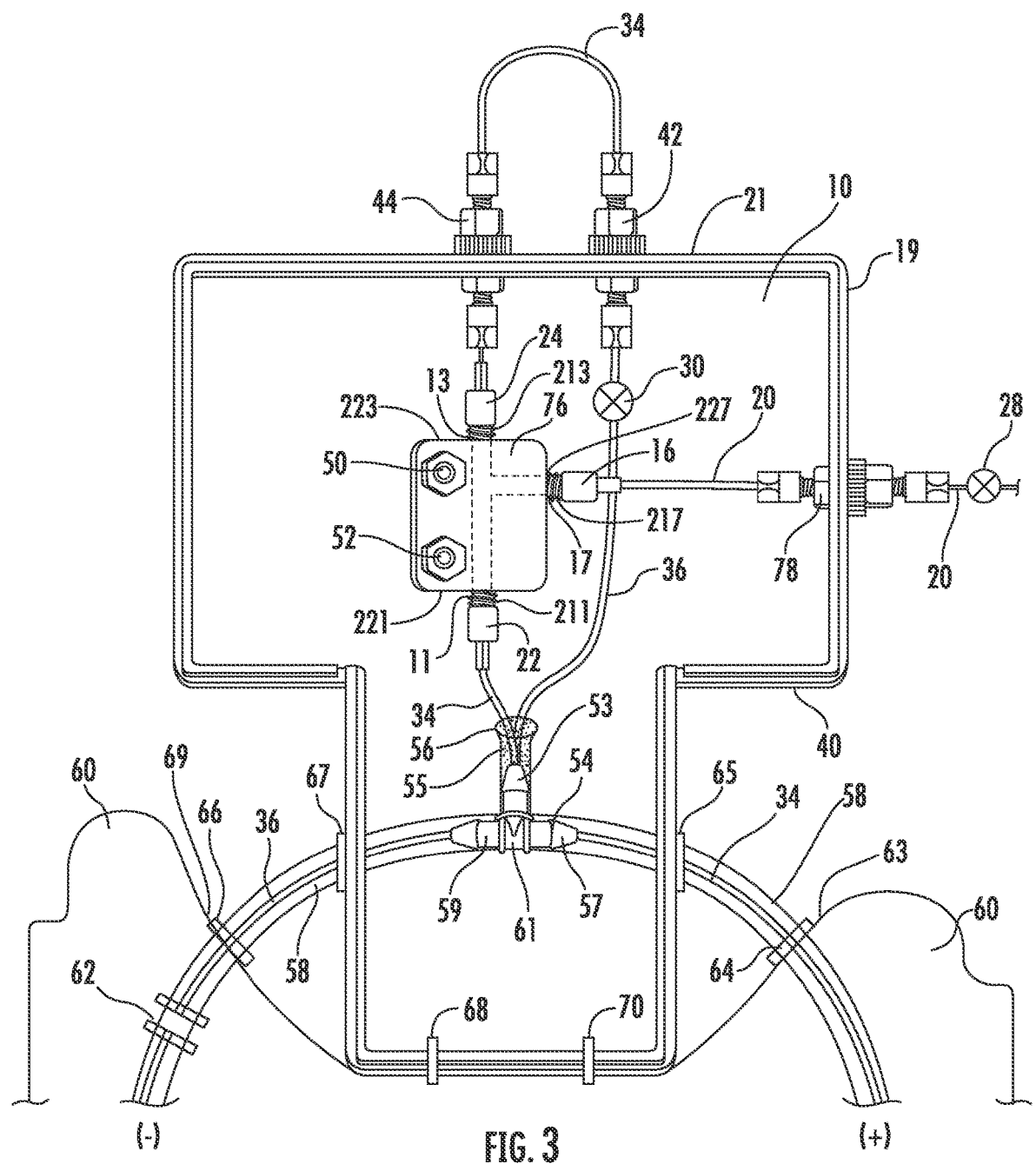
FIG. 3 is a perspective view of an alternate embodiment of FIG. 1.

FIG. 3 illustrates support box 10 harboring a modified analyte concentrator-microreactor device 76 of the present invention. Support box 10 is anchored in a steady and firm position to cartridge-cassette unit 60 of an analytical separation apparatus by screws 68 and 70. Tube 58 is connected to support box 10 by connectors 64, 65, 66 and 67. Separation capillaries or passages 34 and 36 are protected by tube 58. Tube 58 can be heat-resistant. A portion of each separation capillary or passage 34 and 36 is connected to analyte concentrator-microreactor device 76 using port 211 and port 213 for the respective connections using connectors 22 and 24. In order to accomplish this task, the respective portions of separation capillaries or passages 34 and 36 are separated at T-shaped connector 54 and maintained within tube 58 and tubing 56. A sealing material can be used within tubing 56 to hermetically seal capillaries or passages 34 and 36 within tubing 56.

The present invention provides a user-friendly, sample preparation step, which is assembled to work with a capillary electrophoresis apparatus designed to introduce samples from the inlet side of separation capillary or passage 34 positioned at the inlet side 63 of cartridge-cassette unit 60. This portion of the separation capillary or passage 34 acts as a transport capillary or passage permitting the introduction of samples, having constituents or analytes of interest, from inlet side 11 of separation capillary or passage 34 to outlet side 17 of transport capillary or passage 20. A sample containing analytes of interest passes through analyte concentrator-microreactor device 76 housing one or more affinity ligands immobilized to a matrix localized within the elongated portion of analyte concentrator-microreactor device 76, or immobilized directly to the inner surface of the wall or channel of the analyte concentrator-microreactor device 76. Three entrance-exit ports represent the structural configuration of analyte concentrator-microreactor device 76. Port 211 is located at inlet side 221 of the analyte concentrator-microreactor device 76 and is the port of entrance of a sample under study. Separation capillary or passage 34 is connected to analyte concentrator-microreactor 76 by connector 22. Port 217 is located at first outlet side 227 of analyte concentrator-microreactor device 76 and is the port of exit of the sample under study through transport capillary or passage 20, which is connected to analyte concentrator-microreactor device 76 by connector 16 and to exit side 77 of support box 10 by connector 78. Port 213 is located at second outlet side 223 of analyte concentrator-microreactor 76 and is the port of exit of the analytes of interest bound to and released from the affinity ligands immobilized to the matrix positioned at the elongated section of the device or directly to the inner wall or channel of analyte concentrator-microreactor device 76.

Affinity ligands, or molecules that are capable of binding with high affinity to certain moieties of another molecule, making a complementary-pair interaction can be of multiple natures. The most common complementary-pair interactions are antigen-antibody, lectin-sugar, and nucleic acid aptamers that can bind to a wide range of substances. Antibodies, antibody fragments, lectins and aptamers are the preferential affinity ligands that can be immobilized to the matrix of analyte concentrator-microreactor device 76 or directly to its wall surface. The matrix can be made of microstructures made of glass, plastic, ceramic, metallic components, or a combination of various materials. The microstructures can be individually localized within the elongated portion of analyte concentrator-microreactor device 76 in a free-floating arrangement, or they can be connected covalently to each other and to the surface of the inner wall of analyte concentrator-microreactor device 76. The microstructures can also be made of fiber-made monoliths with structures that include aligned fibers, woven matrices, or contiguous fabric structures. The advantages of porous polymers monoliths or sol-gel structures is that they do not need frits to be maintained in place, within the elongated inner portion or channel of analyte concentrator-microreactor device 76, and they can have better operational performance than other microstructures. Individually made microstructures, such as beads, need frits structures or constrictions, in terminal areas of the capillaries, to be held in place.

The dynamics of operation of analyte concentrator-microreactor device 76 containing three entrance-exit ports is different than analyte concentrator-microreactor device 12 containing four entrance-exit ports. Micro-valve 30 should be maintained closed and micro-valve 28 should be open for sample introduction into separation capillary or passage 34. A sample containing analytes of interest is introduced from a vial or container localized at the base of inlet side (not shown) of cartridge-cassette unit 60 and is usually introduced by pressure into separation capillary or passage 34. The sample is passed through analyte concentrator-microreactor 76 by means of separation capillary or passage 34 and exits through capillary or passage 20 to a waste container (not shown). Analytes of interest are retained by affinity ligands immobilized to the matrix of analyte concentrator-microreactor device 76 or its inner surface of the wall or channel. Thereafter, a cleaning buffer or solution is passed through the same path of the sample maintaining micro-valve 30 closed and micro-valve 28 open. Once all unwanted materials and salts have been removed from separation capillary or passage 34 and transport capillary or passage 20, then micro-valves are switched in positions open-closed such that micro-valve 28 is closed and micro-valve 30 is open.

The separation process starts by previously conditioning separation capillaries or passages 34 and 36 with a separation buffer capable of maintaining the integrity of the binding of the analytes of interest and the immobilized affinity ligands, and also maintaining the integrity of the immobilized affinity ligands for repetitive uses. A small plug of an elution buffer or solution is introduced from a vial or container (not shown) localized on the inlet side of separation capillary or passage 34 and at inlet side 63 of cartridge-cassette unit 60. The elution buffer function is to release the analytes of interest bound to the immobilized affinity ligand. Mechanical pressure can be used to push the plug of elution buffer or solution for one, two or more seconds at low pressure, at the beginning of the separation process, followed by electrophoresis, electro-osmotic flow, mechanical pressure, or a combination of electro-osmotic flow and mechanical pressure. The plug of an elution buffer or solution can also contains a chromophore for the simultaneously release and derivatization of the bound analytes of interest. There are several modes of capillary electrophoresis separation and the separation of the analyte of interest can be carried out by any particular separation mode or a combination of them, for example, a combination of immunoaffinity capillary electrophoresis and transient isotachophoresis, or a combination of immunoaffinity capillary electrophoresis and capillary isoelectric focusing.

After separation of the analytes of interest, a process of detection can be carried out at detection point 62, by the use of one or more detector systems at the outlet side of separation capillary or passage 36, or in a longer section of the capillary with the help of a charge-coupled device (CCD) cameras or image sensors. One or more on-line and/or off-line detectors can be positioned at the outlet side of the separation capillary or passage 36, including ultraviolet, fluorescence, laser-induced fluorescence, chemiluminescence, bioluminescence, radiometry, conductivity, electrochemical, nuclear magnetic resonance, mass spectrometer, circular dichroism, Raman-infrared detection, and/or modified version of these detectors. Charge-coupled devices are multichannel array detectors for use with ultraviolet, visible and near-infra light detection. The results obtained by one or more detectors can be further processed by a data acquisition system (not shown).

One or two temperature control systems can be used for the binding and separation processes of the analytes of interest as described in FIG. 1. Once the entire process of separation and data acquisition is finished, the capillaries or passages are cleaned by a cleaning solution followed by an optimization buffer, preparing the transport capillaries and separation capillaries for a new cycle of operation.

Figure 4:
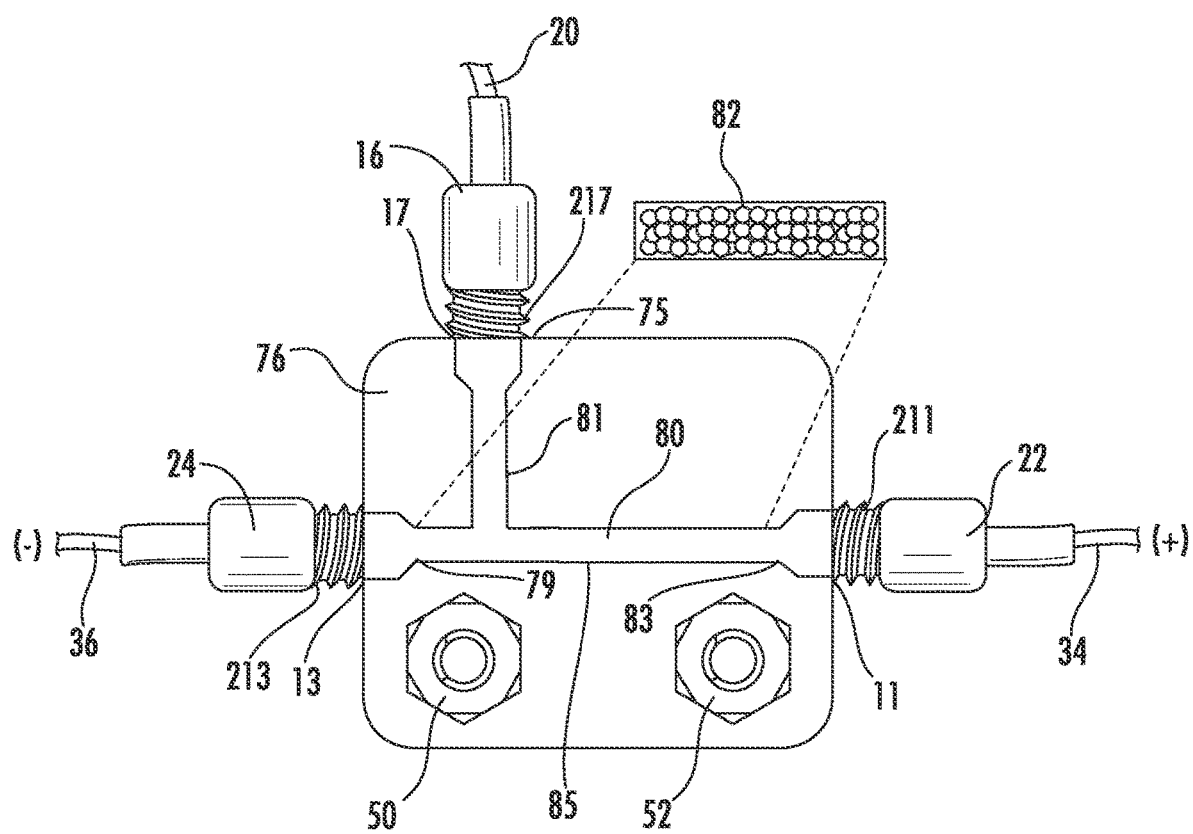
FIG. 4 is an enlarged elevation view of an analyte concentrator-microreactor device shown in FIG. 3.

FIG. 4 illustrates analyte concentrator-microreactor device 76 of the present invention. Analyte concentrator-microreactor device 76 functions as a structural unit composed of three entrance-exit ports where capture, concentration or microreactions occurs. Port 211 of analyte concentrator-microreactor device 76 is the inlet side connection to a portion of the separation capillary or passage 34 using connector 22. Port 213 of analyte concentrator-microreactor device 76 is the outlet side connection to a portion of separation capillary or passage 36 using connector 24. Between port 211 and port 213 is elongated tubular portion or channel 80 serving as the primary place where microstructures or polymeric materials 82 are deposited for the immobilization of affinity ligands. Elongated portion or channel 80 is where the capture, isolation, purification, and enrichment of analytes of interest occur. Elongated tubular portion or channel 80 can be used for immobilizing enzymes for microreactions to occur, or placing or encapsulating cells, subcellular structures, or cellular receptors to carry out metabolic studies and bioactivity studies. Port 217 of analyte concentrator-microreactor device 76 is the outlet side connection to a portion of the transport capillary or passage 20 using connector 16. Port 217 is positioned at upper portion 75 of analyte concentrator-microreactor device 76. Three way junction 85 comprises connection area 79 connected to connection area 81 and elongated portion or channel 80, connection area 81 connected to connection area 79 and elongated portion or channel 80 and connection area 83 connected to elongated portion or channel 80. Preferably, three way junction 85 has a shifted T-shape.

Analyte concentrator-microreactor device 76 is maintained anchored to support box 10 by screws 50 and 52.

Figure 5:
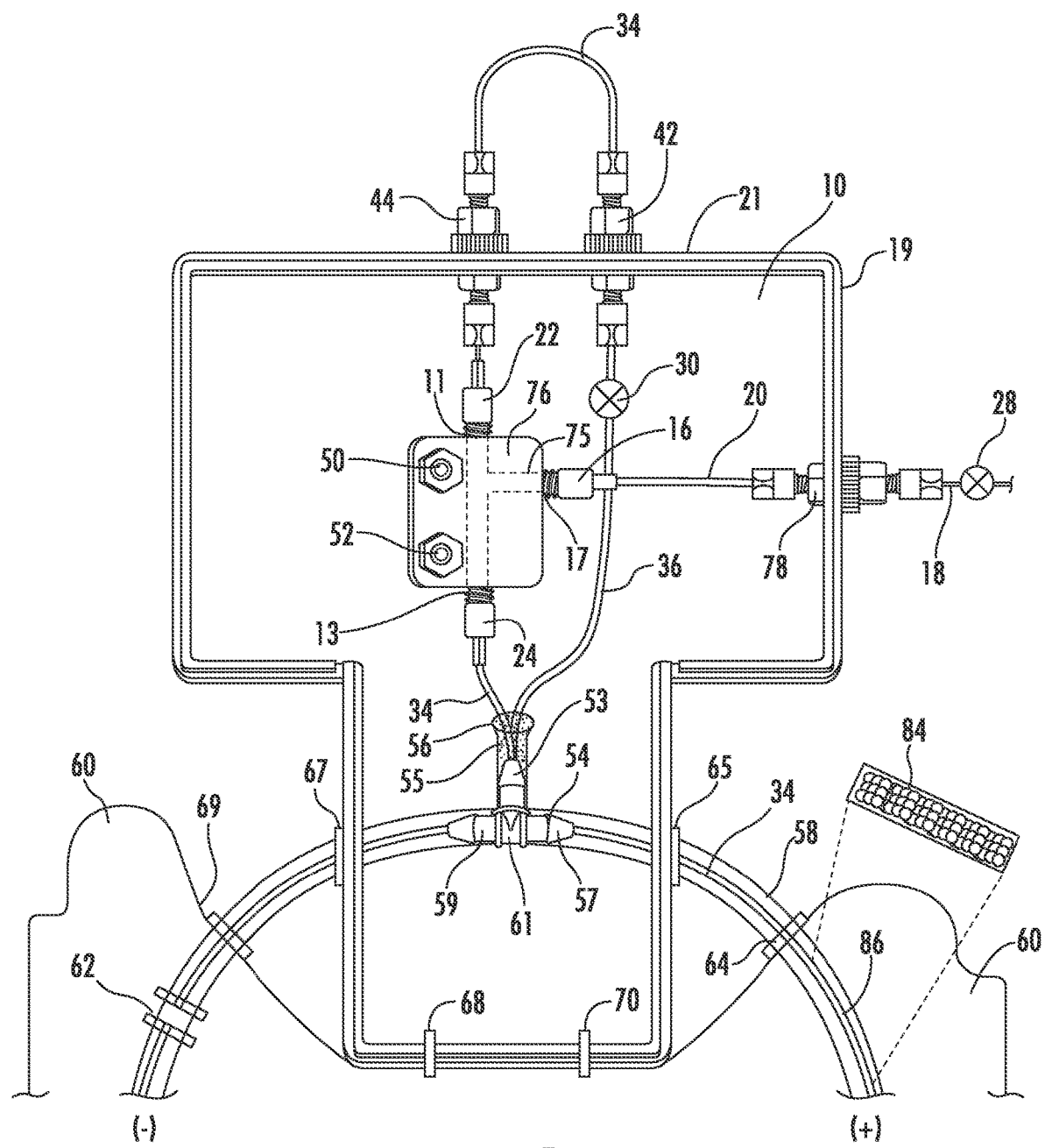
FIG. 5 is a perspective view of the T-shaped support containing a different location for an analyte concentrator-microreactor used in FIG. 3.

FIG. 5 illustrates support box 10 harboring a modified analyte concentrator-microreactor device 76 of the present invention. The description of FIG. 5 is identical to FIG. 3 with the exception that the separation capillary or passage 34 can also be used as an area where an additional analyte concentrator-microreactor device can be localized. Microstructures 84 can be placed within a certain area of the separation capillary or passage 34, preferentially located near the inlet of separation capillary or passage 34. Microstructures 84 are represented by various nano or micrometers in size, and various millimeters or centimeters in length, depending of the internal diameter of separation capillary or passage 34 employed, of free-floating or connected beads, platelets, chips, fibers, filaments, membranes or the like. Individual substrates can be made from glass, plastic, sol-gels, monolithic polymers or other polymeric material, ceramic, or metallic compositions, and mixtures thereof. Coated or otherwise properly oriented immobilized analyte-specific antibodies or other affinity chemistries, including lectins or aptamers, or a combination of them, which are suitable for the capture, purification, separation, quantification and characterization of particular analytes of interest. Analyte concentrator-microreactor device 86 includes an area having microstructures 84. Microstructures 84 can be held in place by porous frit materials, bound to each other or to the internal wall or channel of separation-transport capillary, or by positioning one or two magnets (not shown) when magnetic microstructures are used. One or multiple affinity ligands can be immobilized to the surface of one or more of the various types of matrices incorporated into one analyte concentrator-microreactor device or area, for example, analyte concentrator-microreactor devices 76 or 86, or to more analyte concentrator-microreactor devices or areas for example, analyte concentrator-microreactor devices 76 and 86. Alternatively, one or multiple affinity ligands can be immobilized directly to the surface of one or more of the inner surfaces of the walls or channels serving as one or more analyte concentrator-microreactor devices or areas for example, analyte concentrator-microreactor devices 76 and/or 86. The integrated system composed of support box 10, cartridge-cassette unit 60, hermetically connected separation and transport capillaries or passages 34 and 36 with analyte concentrator-microreactor devices 76 and 86, and micro-valves 28 and 30, can perform multiple analysis, when part of a complete analytical separation apparatus, by capturing, purifying, separating, detecting, quantifying and characterizing the presence of a plurality of analytes for example, three. The affinity ligands can be of the same types for example, three different antibodies for three different analytes of interest, or a combination of antibodies, lectins, or aptamers.

An advantage of the embodiment presented in FIG. 5 is the capability of using one or two analyte concentrator-microreactor devices or areas individually or in conjunction, for example analytical concentrator-microreactor devices 76 and/or 86.

When working individually as an analyte concentrator-microreactor device or area, the operation can be different for a particular application. For example, if analyte concentrator-microreactor device 86 is used as a concentrator, the sample under study containing one or more compounds, analytes or biomarkers of interest is passed from the inlet side of the separation-transport capillary or passage 34 all the way to the exit side of the transport capillary or passage 20 to a waste container (not shown), micro-valve 28 is open and micro-valve 30 is closed. In this case, analyte concentrator-microreactor device 76, with a T-shifted design, is used only as a passage area for the sample to exit through transport capillary or passage 20 to a waste container (not shown). There is no matrix or immobilized affinity ligands in the elongated portion of analyte concentrator-microreactor device 76. It is just a hollow passage. Although this portion of the separation capillary or passage 34 is prone to physisorption or non-specific adsorption of unwanted materials present in the sample under study, it resulted in a negligible amount due to the small size of the separation or capillary or passage 34. Micro-valve 30 prevents the sample from passing through separation capillary or passage 36. Alternatively, separation capillary or passage 34 can be coated with protective chemistries to avoid the binding of unwanted sample materials. The protective chemistries to minimize surface fouling can be additives present in the separation buffer, such as detergents such as for example Tween 20, or bound to the surface of the capillary such as bovine serum albumin blocking step after immobilization of the corresponding affinity ligands, dynamic coatings, or other antiadhesive coating chemistries, such as for example as described by Kim D, Herr A E, Biomicrofluidics, volume 7, doi: 10.1063/1.4816934, 1013.

After the sample is passed through the matrix of analyte concentrator-microreactor device 86, where the analytes of interest can be captured and retained, an appropriate cleaning buffer solution is passed through the same path that passed the sample to remove all unwanted compounds of the sample under investigation that did not bind to the one or more affinity ligands immobilized to the surface of the matrix or walls or inner side of the channels. Once the tubular or channel path system of separation capillary or passage 34 is clean, an appropriate separation buffer, that preserves the integrity of the immobilized affinity ligand and the binding of the analytes of interest and affinity ligands, is passed through the same path that passed the sample and cleaning buffer or solution. Thereafter, the micro-valves are switched in operation. Micro-valve 28 is closed, and micro-valve 30 is open.

The separation buffer is preferentially introduced into separation capillary or passage 34 under pressure controlled by an electronic circuitry, part of the controlling system of the capillary electrophoresis instrument or analytical separation apparatus. Two vials or containers filled with separation buffer are placed on the base of cartridge-cassette unit 60, one vial is positioned on the inlet side of the base and another vial is positioned on the outlet side of the base to make a closed operating system, comprising separation capillary or passage 34 connected to analyte concentrator-microreactor device 76, which in turn is connected to separation capillary or passage 36. Micro-valve 28 continues to be closed, and micro-valve 30 continues to be open.

Once the separation buffer is in place, filling the entire separation capillaries or passages 34 and 36, and analyte concentrator-microreactor device 86, a process of elution or release of the bound analytes of interest from analyte concentrator-microreactor 86 is performed. A small volume or plug of elution buffer or solution is introduced from the inlet side of separation capillary or passage 34 preferentially by small pressure, but also can be introduced by electro-osmotic flow. The plug of an elution buffer or solution is composed of a low pH buffer, high pH buffer, an analog competing for the binding, a chaotropic agent that disrupt hydrogen bonding between water molecules such as urea or guanidine, or a combination of them, including the presence of a detergent, a reducing agent or other chemical substances. The plug of an elution buffer or solution can also contains a chromophore for the simultaneously release and derivatization of the bound analytes of interest.

Thereafter the introduction of a plug of an elution buffer, a process of separation is performed in the separation capillary or channel, electrically, by electro-osmotic flow, mechanical pressure, or a combination of electro-osmotic flow and mechanical pressure. In open tubular capillary when the capillary is filled with buffer, the preferential method of separation is electro-osmotic flow or a combination of electro-osmotic flow and mechanical pressure. When the separation capillary is filled with a polymeric material, such as monolithic solid phase or sol-gels or similar solid phases, the preferential method of separation is by electrical charge. Mechanical pressure, such is the case of capillary high-pressure chromatography, is the method of choice for separation when the capillary is filled with a solid support made of glass or plastic beads, or a polymeric material.

As the plug of elution buffer or solution keep advancing within the separation capillary or passage 34, and passing through the elongated portion of analyte concentrator-microreactor device 86, release of all analytes of interested bound to one or more affinity ligands immobilized to the matrix or inner wall or channel of analyte concentrator device 86 occurs. Detection of one or more released analytes of interest occurs at detection point 62 positioned at the outlet side of the separation capillary or passage 36 on outlet side 69 of cartridge-cassette unit 60.

In another embodiment of the present invention, the integrated system of T-shaped support box, cartridge-cassette unit 60, transport and separation capillaries or passages 34 and 36 hermetically connected to analyte concentrator-microreactor device 76, and micro-valves 28 and 30, can be used with two analyte concentrator-microreactor devices 76 and 86. For example, analyte concentrator-microreactor device 86 can perform as a concentrator and analyte concentrator-microreactor device 76 can perform as a derivatization site for derivatizing substances released from analyte concentrator-microreactor device 86. As bound analytes of interest are released from analyte concentrator-microreactor device 86 and separate in separation capillary or passage 34, they will pass analyte concentrator-microreactor device 76 to which chomophores are retained by affinity ligands immobilized to the matrix or inner surface of the elongated region of analyte concentrator-microreactor device 76. Thereafter, another plug of an elution buffer or solution is introduced from the inlet side of the separation capillary or passage 34 to release the analyte-chromophore complex of interest bound to the affinity ligand. The process of separation of the tagged or derivatized analytes of interest through capillary or passage 36 is the same as previously described for FIG. 1 and FIG. 3.

In another embodiment of the present invention, analyte concentrator-microreactor device 86 can act as a microreactor having proteolytic enymes immobilized to the surface of the matrix or inner surface of the capillary or channel. Proteins can be cleaved into peptides as they pass analyte concentrator-microreactor device 86, and peptides can continues separation within separation capillary or passage 34 and separation capillary or passage 36 until detection point 62. Alternatively, peptides separated within separation-transport capillary 34 can be derivatized within analyte concentrator-microreactor device 76 by chromophores bound to the affinity ligands immobilized to the matrix or directly to the inner surface or channel of analyte concentrator-microreactor device 76. The process of elution, separation and detection of derivatized analytes of interest is the same as described previously.

Still another embodiment of the present invention is to use analyte concentrator-microreactor device 86 for metabolic studies or bioactivity studies. Encapsulated cells or cellular receptors within the area of analyte concentrator-microreactor device 86 can release metabolites that can further be separated within separation capillary or passage 34 and separation capillary or passage 36 until detection point 62. Alternatively, released and separated metabolites can be derivatized within analyte concentrator-microreactor device 76, further eluted and separated within separation capillary or passage 36 until detection and quantification at detection point 62.

Analyte concentrator-microreactor device 86 can be adapted (not shown) for cellular or cellular receptor encapsulation as described in U.S. Pat. No. 9,482,602, which is incorporated by reference in this disclosure.

Figure 6:
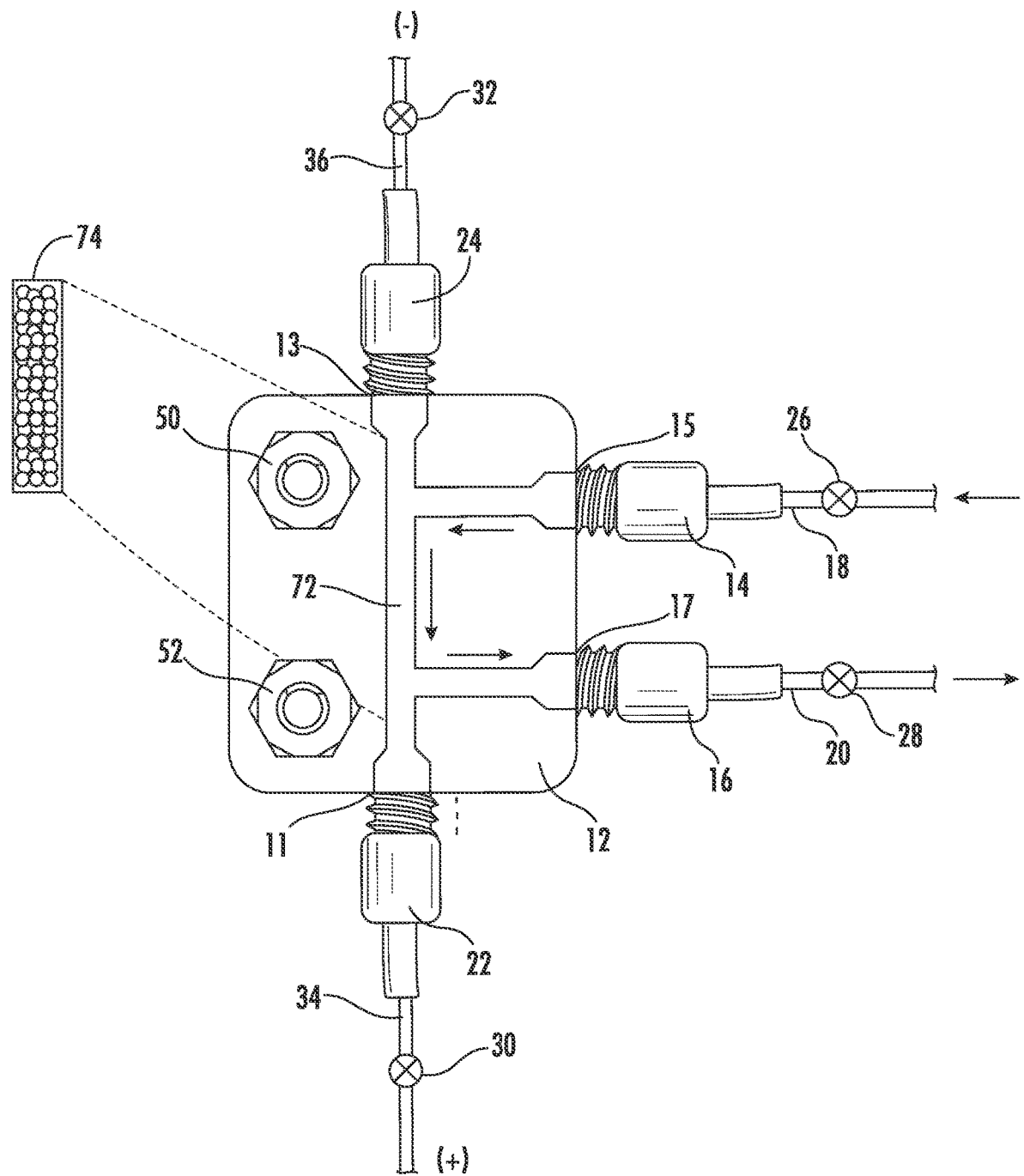
FIG. 6 is a perspective view of a method of using the analyte concentrator-microreactor (ACM) device shown in FIG. 1.

FIG. 6 illustrates a protocol or method to be used with an embodiment of analyte concentrator-microreactor (ACM) device 12. The purpose of the protocol is to provide a standardized guideline of operation that ensures error-free results. Matrix 74, containing a solid support to which selective or non-selective affinity ligands are preferentially immobilized covalently to their surfaces in a well-oriented position, is localized in elongated tubular portion or channel 72. The solid support material of matrix 74 can be micro- or nano-beads or particles uniformly or irregularly made of plastic, glass, ceramic, or polymeric material. The beads can be composed of a defined chemical structure and porosity, or they can contain a mixture of other materials including some metallic components that transform them into magnetic particles. Whole antibody molecules, antibody fragments, including single chain antibodies, and domain antibodies, represent a class of affinity ligands. Affinity ligands are molecules that are capable of binding with very high affinity to either a moiety specific. These biomolecules can be natural or engineered in a laboratory. The isolation of a single molecule from simple or complex mixtures remains a complex challenge in many areas, including clinical laboratory, pharmaceutical industries, food-beverage industries, forensic sciences, and other fields. Many other large diversity affinity ligands are also available for building a capture system that is simultaneously effective and specific. Such affinity ligands, other than antibodies, are lectins (binding sugar moieties), aptamers (binding DNA, RNA, or proteins). Also, polypeptides from phage display, structures derived from natural ankyrin repeats, and stefin-based scaffolds are the most known protein-based affinity ligands. In general any chemical structure of different size and configuration, and having high affinity ligand properties, can be considered an affinity ligand, including combinatorial libraries of small and large compounds, and nucleic acids, lipids and carbohydrates.

There are many factors to be considered in order to obtain reproducible results. One important factor is to preserve the integrity of the immobilized affinity ligands. The immobilized affinity ligands must withstand at various pH, temperatures, and the presence of different salt concentrations, maintaining the affinity ligand stable and intact once they are immobilized to the solid matrix support. Any molecular change and/or degradation of the immobilized affinity ligand may influence the integrity of the molecule and the quality of the binding properties. Chemical modification to the affinity ligand can be introduced to further enhance its stability and its resistance to degradation by proteases, nucleases, and other compound present in a biological environment. Another crucial factor is to maximize the density and affinity capture of target analytes at the surface of the beads or inner wall. For this, it is necessary to have the proper orientation of the immobilized affinity ligands. The performance of binding interaction between the immobilized affinity ligand and the target antigen or analyte depend entirely on the best orientation, which is a key factor to maximize the capturing potential of the immobilized antibody or another affinity ligand, or a combination of two or more affinity ligands. Physical adsorption of antibodies onto traditional immunoassay solid supports, such as polystyrene, occurs via hydrophobic and electrostatic interactions. While this method offers the simplest attachment pathway, it is uncontrollable, and antibodies are usually immobilized in a randomly oriented manner, denatured, or displaced in later washing steps. Covalent attachments to surfaces, via a particular functional group, usually results in improved antibody density and capture capacity. It has been found that the activity of immobilized antibodies varies sensitively between different immobilization chemistries and the antibodies with more accessible Fab domains, or primary binding sites, to antigens, exhibit higher activity than randomly immobilized antibodies.

Suitable chemical methods to crosslink covalently well-oriented affinity ligands to surfaces, include electrochemical, thermal and photo-crosslink protocols. The immobilization of an affinity ligand can be made directly on the surface of the constituents of matrix 74 or directly to the inner surface of elongated tubular portion or channel 72. Alternatively, other proteins, polymers or materials can be immobilized first to the surfaces of matrix 74 or elongated tubular portion or channel 72, and then the affinity ligands can be immobilized to these chemical bridges. Protein A, protein G, protein L, and other surfaces, usually expressed by pathogenic bacteria, are well known to bind immunoglobulin and have been widely exploited in antibody purification strategies. The binding of protein A to IgG varies for the different IgG subclasses. These proteins (proteins A, G, and/or L) can be immobilized to matrix 74 or elongated tubular portion or channel 72, followed by a non-covalent affinity binding to immunoglobulin G (IgG).

Once matrix 74 has been positioned in elongated tubular portion or channel 72 of analyte concentrator-microreactor (ACM) device 12, containing one or more immobilized affinity ligands on the beads, monolithic polymer or directly to the wall of the channel, an optimal buffer solution can be introduced through transport capillary or passage 18, passing through the area where matrix 74 is positioned, and exiting through transport capillary or passage 20, as indicated by the arrows shown in FIG. 6. If matrix 74 is composed of free-floating beads, it is necessary to confine them within a restricted space by pressure-resistant frit structures or constricted capillaries, to avoid leakage of the beads out of the confined space. Polymeric monolithic or sol-gel structures may not need frits, and in case of using magnetic beads, one or more magnets can be positioned in the outer side of analyte concentrator-microreactor (ACM) device 12, on both sides of the area of elongated tubular portion or channel 72 (not shown). It is possible to position a rotating magnet to allow for a constant movement of the magnetic beads (not shown).

In order to protect the integrity of the inner surface of the separation capillary or passage 36, micro-valves 30 and 32 must be closed and micro-valves 26 and 28 must be open. After matrix 74, positioned in elongated tubular portion or channel 72, has been equilibrated with the optimal pH, a sample containing the target antigen or analyte can be introduced into the system following the same protocol performed for the optimization buffer. After the sample has been introduced into analyte concentrator-microreactor (ACM) device 12, it is expected that the target antigen has been captured and retained by the immobilized antibody, or by one or more additional immobilized affinity ligands. Components that are present in a simple or complex sample may nonspecifically bind during the passage from the inlet side of transport capillary or passage 18 to the outlet side of transport capillary or passage 20 to the inner surface of transport capillary or passage 18 or 20, or even to certain sites of matrix 74, including the inner surface of elongated tubular portion or channel 72. Therefore, after passing the sample through analyte concentrator-microreactor (ACM) device 12, a washing or cleaning solution is passed through the inlet side transport capillary or passage 18 to the outlet side of transport capillary or passage 20 to remove all unwanted materials bound non-specifically. Again, an optimization buffer is passed through analyte concentrator-microreactor (ACM) device 12 to prepare the captured and retained target antigen(s) or analyte(s) to be released from the immune complex. Both optimization buffer and washing or cleaning solutions must be mild enough to maintain the integrity of the immobilized antibodies, but permitting also maximum binding affinity between the immobilized antibody and its correspondent target antigen or analyte.

At this stage, micro-valves 26 and 28 are closed and micro-valves 30 and 32 are open. The operation of closing and opening of the micro-valves can be preferentially carried out by a collection of instructions by computer-control system. A separation buffer is introduced from the inlet side of the separation capillary or passage 34 to the outlet side of the separation capillary or passage 36. The release of the bound antigens or analytes from analyte concentrator-micro (ACM) device 12, or process of elution, is preferentially carried out by applying a plug or small amount of an elution buffer or solution. Since the antibody-antigen binding usually is most efficient in aqueous buffers at physiological pH and ionic strength; consequently, elution often can be accomplished by either by raising or lowering the pH of the buffer or solution, or by altering the ionic state to disrupt the binding interaction. Many chemical substances can be used as components of the elution buffer or solution. For example, high concentrations of urea, sodium or ammonium thiocyanate, guanidine-HCl, lithium chloride, dioxane, ethylene glycol, and other chemicals can be used for elution. Competition for the binding using analog substances can also be used. For example, elution of lectins and sugars, chelated divalent metals and histidine tags, boronate/cis-diol ester formation, substrates and enzymes can require unique elution conditions. Constituents of the elution buffers are preferentially made with glycine, citric acid, triethylamine, thriethanolamine, Tris-acetate, and other chemicals. It is possible to add to the elution buffer or solution a chromophoric substance with the purpose to elute and derivatize the target analyte bound to the immobilized affinity ligand. Derivatization of the target analyte can also be performed on-line after the bound analytes are released from analyte concentrator-microreactor (ACM) device 12, into the separation capillary or passage 36. This process is known as post-column detection.

Although the use of highly selective affinity capture-selectors, such as antibodies, is the first choice for applications in clinical diagnosis, other types of interactions are used as well. Secondary interactions can be used individually, or in various combinations. The most common interactions are hydrophobic, ionic, hydrogen bonding, and coordination interactions.

The ideal situation is to capture and isolate one expected specific target analyte from rich and complex sources of human chemical-biochemical entities; however, it has been found that using the same experimental conditions unexpected binding analytes can occur. Using a two-dimensional technique such as LACE, for capturing and separation, unexpected analyte (s) can be found from a simple interference, which can be a new biomarker of a physiological process or an indicator of a disease state. This unexpected analyte(s) can by no means be possible to be identified when using only a one-dimensional technique, such as ELISA.

The process of elution starts at the inlet side of separation capillary or passage 34. The plug of elution buffer or solution is preferentially introduced into separation capillary or passage 34 by mechanical pressure, electro-osmotic flow, or by a combination of mechanical pressure and electro-osmotic flow. Once the one or more bound analytes to the immobilized affinity ligand are released by the action of the content of the plug of elution buffer or solution, as it passes the length of elongated tubular portion or channel 72 of analyte concentrator-microreactor (ACM) device 12, containing matrix 74, a process of separation of the released analytes occur in separation capillary or passage 36. The separated analytes can be the expected single analyte, or the single analyte and its metabolites, or isomers of the analyte, or even some unrelated analytes. If a chromophoric substance is added to the elution buffer or solution, the separated analyte(s) are expected to be derivatized or conjugated, having different selectivity properties than their original counterparts, with increased detection sensitivities.

The separation of the analyte(s) in separation capillary or passage 36 can be monitored during the entire process of separation or at the outlet side of separation capillary or passage 36. The detector used for detection of the analyte(s) can be a single one, or it can be two or more. UV absorption is by far the most common detection mode in capillary electrophoresis. For compounds that do not exhibit UV absorption, indirect detection can be applied. An absorbing co-ion is added to the background electrolyte (GGE) or separation buffer or solution, and this is displaced by the analyte, yielding a negative peak rather than the traditional positive peak observed with other compounds that exhibit UV absorption. Fluorescence and laser-induced fluorescence detection are more sensitive methods. A few substances exhibit intrinsic fluorescence detection; therefore, there is no need for conjugation to a chromophoric substance. For those substances that do not exhibit intrinsic fluorescence, a wide range of derivatization reagents are commercially available. The appropriate excitation wavelength should be selected for the target analytes. Excitation sources that allow flexible wavelength selection are xenon, mercury-xenon, and deuterium lamps. Light-emitting diodes (LEDs) can be used as an excitation source, which have advantages due to their small dimensions, stable output, and low costs. Other detectors used with capillary electrophoresis are conductivity, electrochemistry, chemi- or bioluminescence, mass spectrometry, circular dichroism, nuclear magnetic resonance, surface-enhanced resonance Raman spectroscopy, radioactive, charge-coupled detector, and others.

The resulting electropherogram of the captured, purified, concentrated and separated analyte(s) can be quantified by calculating their peak areas using a data acquisition system. Migration time of each separated analyte(s) can provide additional information when using internal standards. Structural data can be obtained with detectors such as mass spectrometry or nuclear magnetic resonance. In the case of proteins, capillary isoelectric focusing, which is one of several modes of capillary electrophoresis, can provide information on the isoelectric point of a protein.

Figure 7:
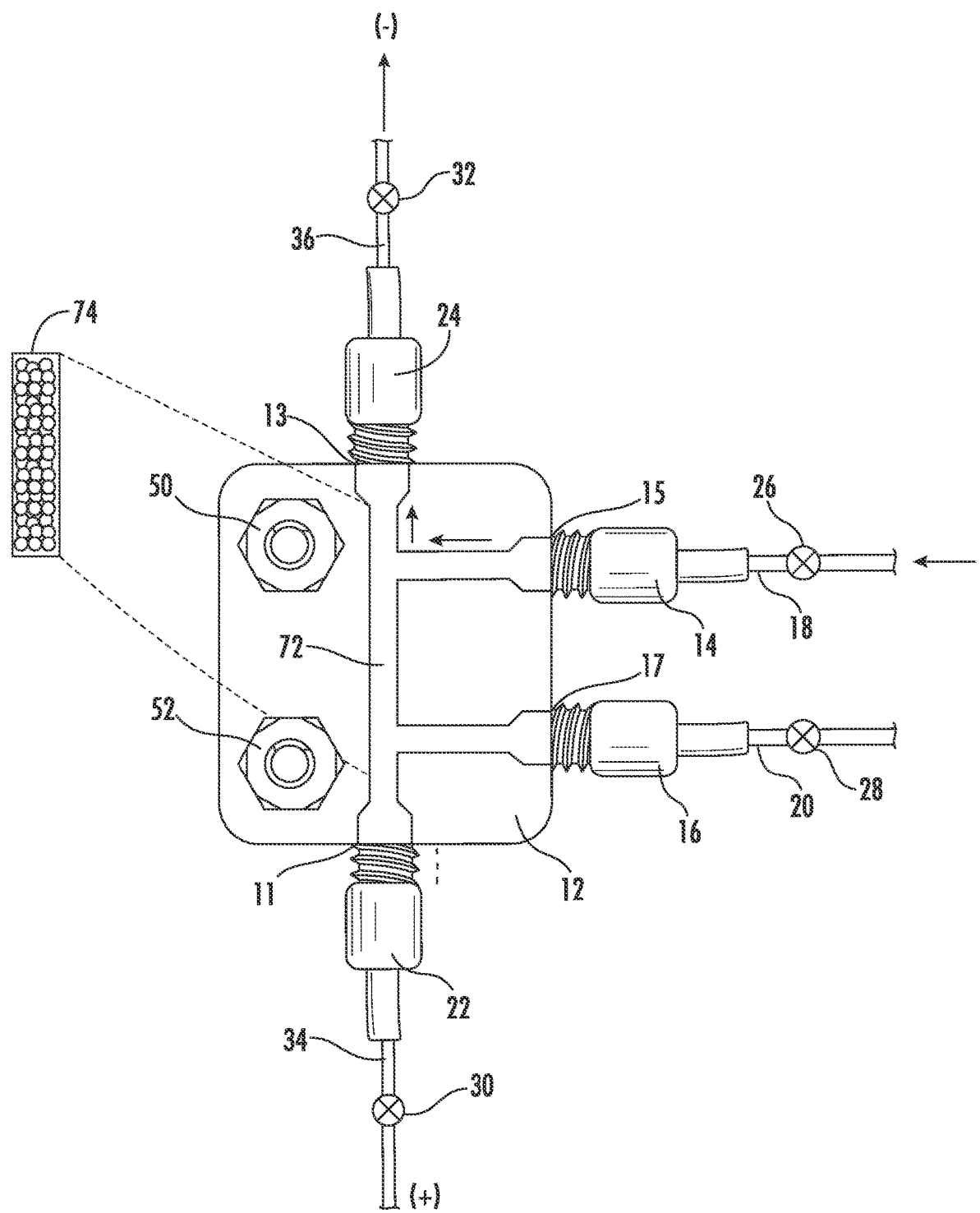
FIG. 7 is a perspective view of a method of using the analyte concentrator-microreactor (ACM) device shown in FIG. 1.

FIG. 7 illustrates an additional protocol or method to be used with an analyte concentrator-microreactor (ACM) device 12. The purpose of this protocol is to provide a standardized guideline of operation that ensures the maintenance of the integrity of the antibodies (or other affinity ligands) immobilized to matrix 74. This process is accomplished by having a separation capillary or passage 36 composed of two types of separation buffers, background electrolytes, or separation solutions: one optimal buffer for the binding step, and one optimal buffer for the separation step.

Ideally, one separation buffer can be used for the capturing of the target analyte(s) to matrix 74, and for the separation the released analytes in separation capillary or passage 36. It has been found that many times the optimal separation buffer used for capturing the target analyte(s), and maintaining the integrity of the immobilized affinity ligand, is not optimal for the separation of the released analyte(s) that were captured and bound to matrix 74. For example, to obtain optimal separation of certain analytes chemical substances may be needed which may destroy the integrity of the antibodies immobilized to matrix 74. Such chemical substances can be urea, sodium dodecyl sulfate, Triton X-100, Tween 20, guanidine-hydrochloric acid, sodium hydroxide, hydrochloric acid, trifluoroacetic acid organic solvents (methanol, acetonitrile), and many other chemicals or a combination of them. Chemical substances that may improve the separation of many molecules using on-column detectors, such as ultraviolet or fluorescence, may not be optimal chemicals for detectors such as a mass spectrometer.

Mass spectrometry is a qualitative and quantitative analytical technique for detection. When applied to biological samples, the power of mass spectrometry lies in its selectivity toward the identification and quantification of compounds. It has been found that mass detection is not completely without problems that can compromise or invalidate results. One important factor that can affect the quantitative performance of a mass detector is ion suppression. The main cause of ion suppression is a change in the spray droplet solution properties caused by the presence of nonvolatile or less volatile solutes. Another factor causing ion suppression is the mass and charge of individual analytes. It has been shown that molecules with higher mass suppress the signal of smaller molecules and the more polar analytes are more susceptible to suppression. There are several options that can be used to minimize or correct for ion suppression. For example, the use of weaker acids such as acetic, formic, or hexafluorobutyric acid may substitute other acids such as trifluoroacetic acid. Also, the addition of 2-(2-methoxyethoxy)ethanol to the separation buffer can serve as a signal enhancer to eliminate the ion-suppressive effect of acetate anions.

After using the protocol described in FIG. 6, where the sample containing one or more analytes of interest is passed through the matrix (solid support-antibody) localized within analyte concentrator-microreactor (ACM) device, and excess amount of unwanted substances have been eliminated, the release of the bound analyte(s) is subjected to a process of elution. However, for the process of elution to occur, an optimal separation buffer must be introduced into the separation capillary or passage 36 via transport capillary or passage 18, away from matrix 74 localized in elongated tubular portion or channel 72 of analyte concentrator-microreactor (ACM) device 12. The protocol described in FIG. 7 protects the integrity of the antibody (or other affinity ligand) immobilized to matrix 74, localized within elongated tubular portion or channel 72 of analyte concentrator-microreactor (ACM) device 12, or directly to the inner wall of analyte concentrator-microreactor (ACM) device 12. This is because the optimal separation buffer is introduced from a different direction where matrix 74 is positioned. Microvalves 28 and 30 must be closed and valves 26 and 32 must be open. The separation buffer is introduced via transport capillary or passage 18 and exiting separation capillary or passage 36 all the way to the end of the outlet side of the separation capillary or passage 36. Once separation capillary or passage 36 has been filled with the optimal separation buffer, valves 26 and 28 must be closed and valves 30 and 32 must be open. A plug, or small amount of an elution buffer, is introduced into separation capillary or passage 34 from the inlet side of separation capillary or passage 34 by electrophoresis migration, or mechanical pressure, or a combination of electro-osmotic flow and mechanical pressure. After the introduction of the plug into the inlet side of separation capillary or passage 34 from an elution buffer container, a mild buffer that will not affect the integrity of the immobilized affinity ligand is positioned in a separate container. Separation will start when the power supply is turned-on and the separation protocol will proceed by electrical migration, electro-osmotic flow, or just mechanical pressure, or a combination of electro-osmotic flow and mechanical pressure. The mild buffer will push the elution plug until it passed through concentrator-microreactor (ACM) device 12 and it will release all bound materials from matrix 74. Separation of the released analytes may happen primarily in separation capillary or passage 36, using the first introduced optimal separation buffer via transport capillary or passage 18, and still be capable of yielding mass spectrometry results before the mild buffer reaches the mass spectrometer. If this protocol may cause some problems with generating optimal mass spectrometry data, an alternative separation process is described in FIG. 8.

FIGS. 8A-8F illustrate an additional protocol to be used with an embodiment of analyte concentrator-microreactor (ACM) device 12. The purpose of this protocol or method is to provide a design by which the two buffer systems described in FIG. 7 can operate with an additional high-voltage power supply.

The first step consists of the immobilization of one or more affinity ligands to the surface of a solid-support matrix 74 prior to matrix 74 being deposited into elongated tubular portion or channel 72 of analyte concentrator-microreactor (ACM) device 12. Matrix 74 can be positioned with the use of frits if the solid support is composed of non-magnetic beads. If the solid support is composed of beads containing some metal elements, then the matrix can be positioned with the use of one or more fixed magnets, or with the use of a magnet in motion using a mechanical system for rotation of the magnetic beads. The fixed or rotating magnets are positioned in the external sidewall of the ACM device. Alternatively, the matrix can be made of a continuous block of porous structures or monoliths, or by restrictions points, or by interconnecting the beaded microstructures to each other and to the surface of the wall of the inner cavity or channel of the ACM device.

Figure 8A:
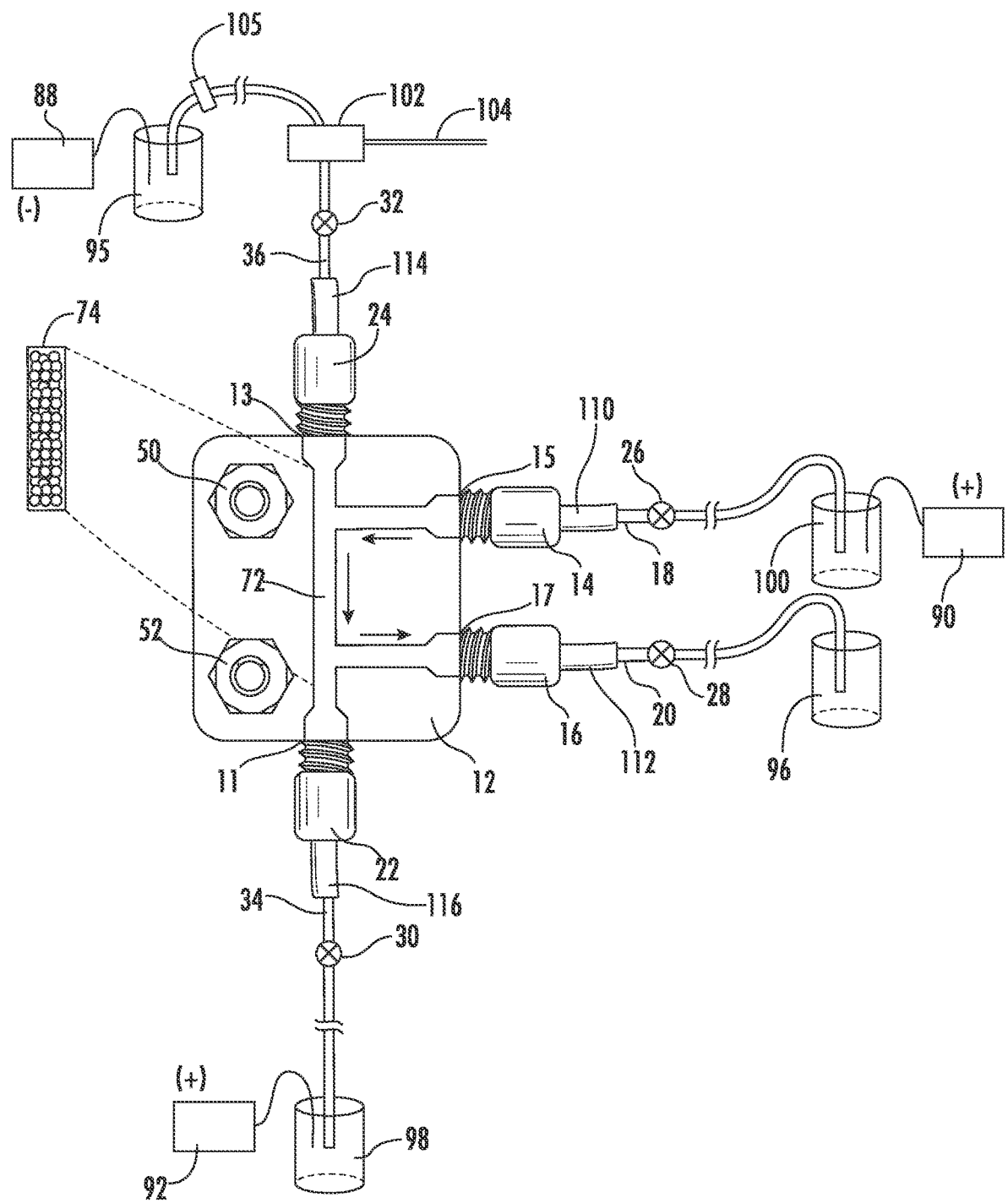
FIGS. 8A-8F are perspective views of a method of using the analyte concentrator-microreactor (ACM) device including a voltage supply.

After using the protocols described in FIGS. 6 and 7, where the washing buffer, conditioning buffer, the sample containing one or more analytes of interest is passed through matrix 74 (solid support-antibody and/or other affinity ligands) localized within analyte concentrator-microreactor (ACM) device 12, and a cleaning buffer is applied to remove the excess amount of sample and unwanted substances as shown in FIG. 8A. The sample and the washing buffer or solution, are introduced, usually mechanically, through the inlet side of transport capillary or passage 18 from container 100, following the direction of the arrows, all the way to container 96 localized in the outlet side of transport capillary or passage 20. Container 100 can be interchangeably used separately for samples and buffers, utilizing a corresponding container for each sample and buffer. This process of sample and buffer introduction is performed when micro-valves 30 and 32 are closed and micro-valves 26 and 28 are open. The washing or cleaning buffer or solution must be a buffer that preserves the integrity of the immobilized affinity ligands.

Figure 8B:
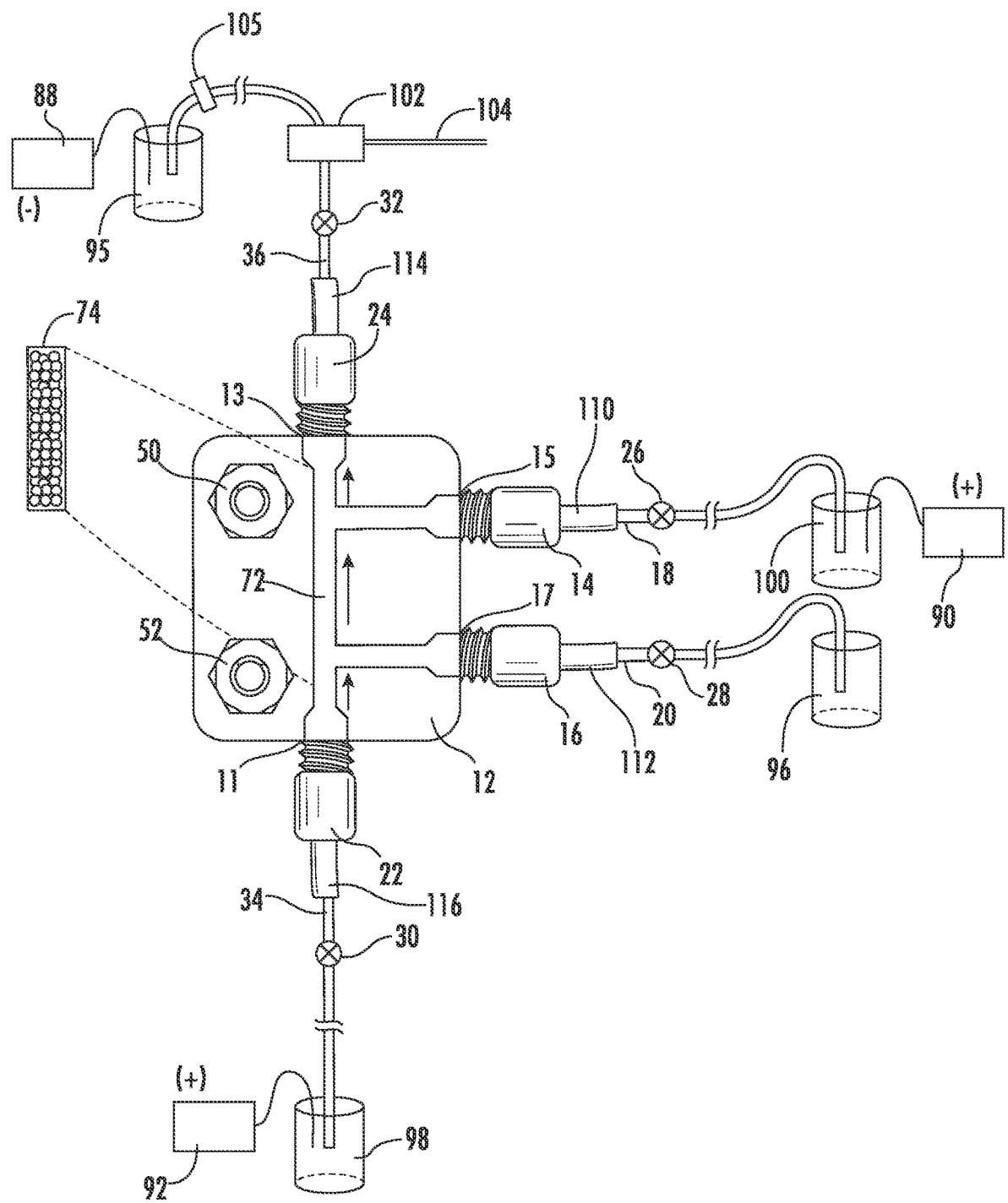

Once the excess amount of sample and unwanted substances are removed from the system, a process of elution or release of the bound analyte(s) from matrix 74 starts. Prior to this process, micro-valves 26 and 28 are closed and micro-valves 30 and 32 are open as shown in FIG. 8B. A separation buffer is introduced, from container 98 usually by mechanical pressure, from the inlet side of separation capillary or passage 34, all the way through ACM device to the outlet side of separation capillary or passage 36. This separation buffer must also be capable of preserving the integrity of the affinity ligands immobilized to the solid support matrix.

Figure 8C:
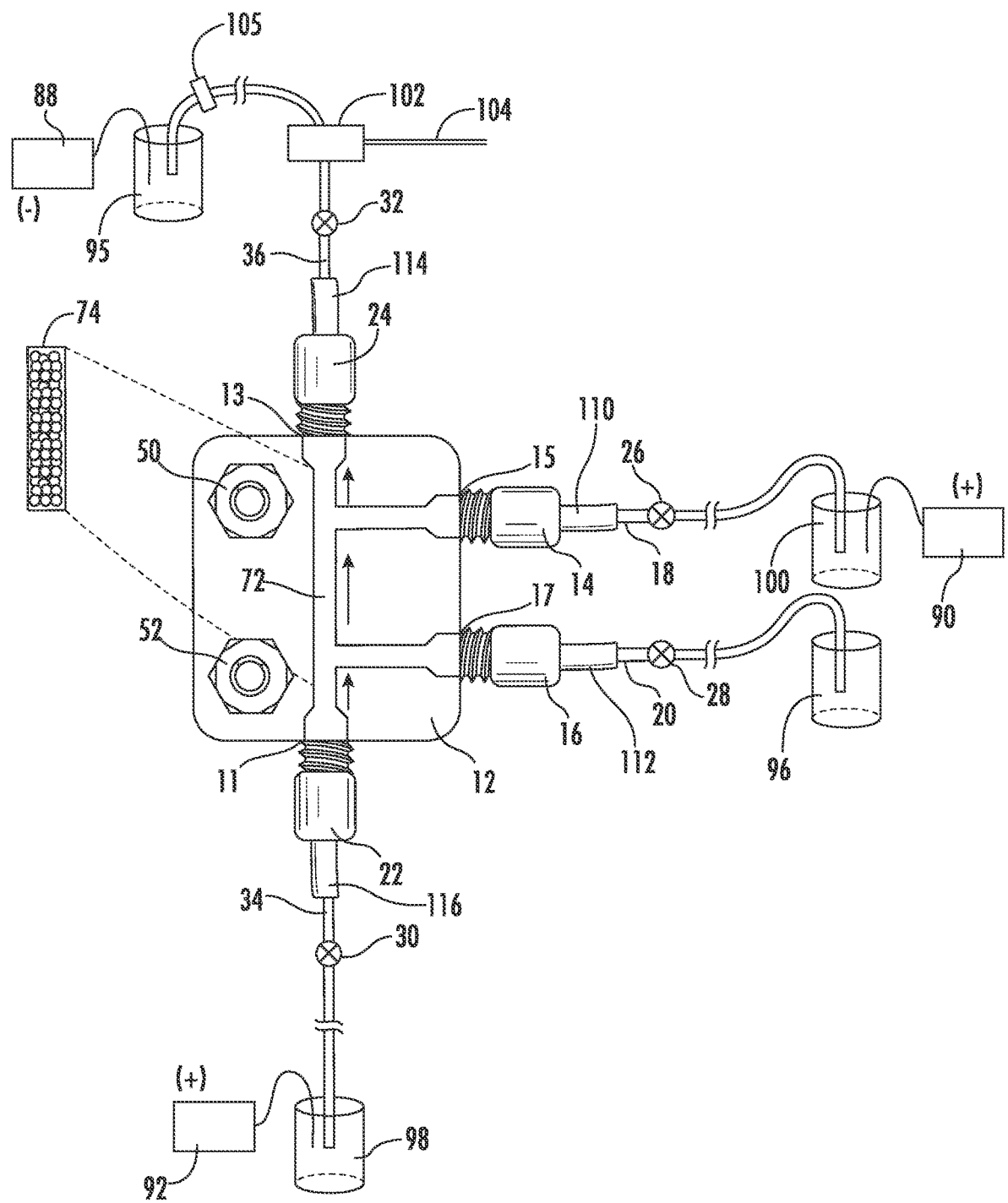

A small volume or a plug of an elution buffer or solution is introduced from container 98 the inlet side into separation capillary or passage 36 by electro-osmotic flow, mechanical pressure, or a combination of electro-osmotic flow and mechanical pressure until it passed the outlet side of analyte concentrator-microreactor (ACM) device 12 device as shown in FIG. 8C. To confirm the release of the one or more analytes from matrix 74, and analyte(s) have reached separation capillary or passage 36, on-line detector 102 is positioned just outside the ACM device. On-line detector 102 can be connected to fiber optic 104 bridging on-line detector 102 to a photomultiplier system that is coupled to a computerized monitor system. This process of electrical connection is carried out when separation capillary 34 is immersed into container 98, which is connected through a platinum-iridium wire to a positive-polarity high-voltage power supply 92. This can be the high-voltage side of the system. The outlet side of separation capillary or passage 36 is immersed into container 95 that is connected through a platinum-iridium wire to a grounding system. Alternatively, the polarity of the system can be reversed, where negative-polarity high-voltage power supply 88 is connected via a platinum-iridium wire to container 95 and to separation capillary or passage 36. For example positive-polarity high-voltage power supply 92 and negative-polarity high-voltage power supply 88 can apply a voltage in the range of about 2,000 volts to 30,000 volts, and an electrical current in the range of about 10 microamperes to 200 microamperes. An appropriate cooling-heating system can be used to maintain a fixed temperature to yield consistent and reproducible results. Uncontrolled temperatures distort the separation and may denature the biomolecules under analysis. One or more detectors, 105 off-line or on-line, can be located in the outlet side of the separation capillary or passage 36 for monitoring the separated capillaries. On the other hand, a charge-coupled device (CCD) camera can be used as a detector throughout the entire separation capillary, after analyte concentrator-microreactor (ACM) device 12, to continuously monitoring the entire separation process of the eluted analytes. The separation process starts immediately after the plug of separation buffer or elution is introduced into the inlet side of the separation capillary or passage 34. Container 98 can be interchangeably used separately for samples and elution buffers, utilizing a corresponding container for each sample and buffer.

Figure 8D:
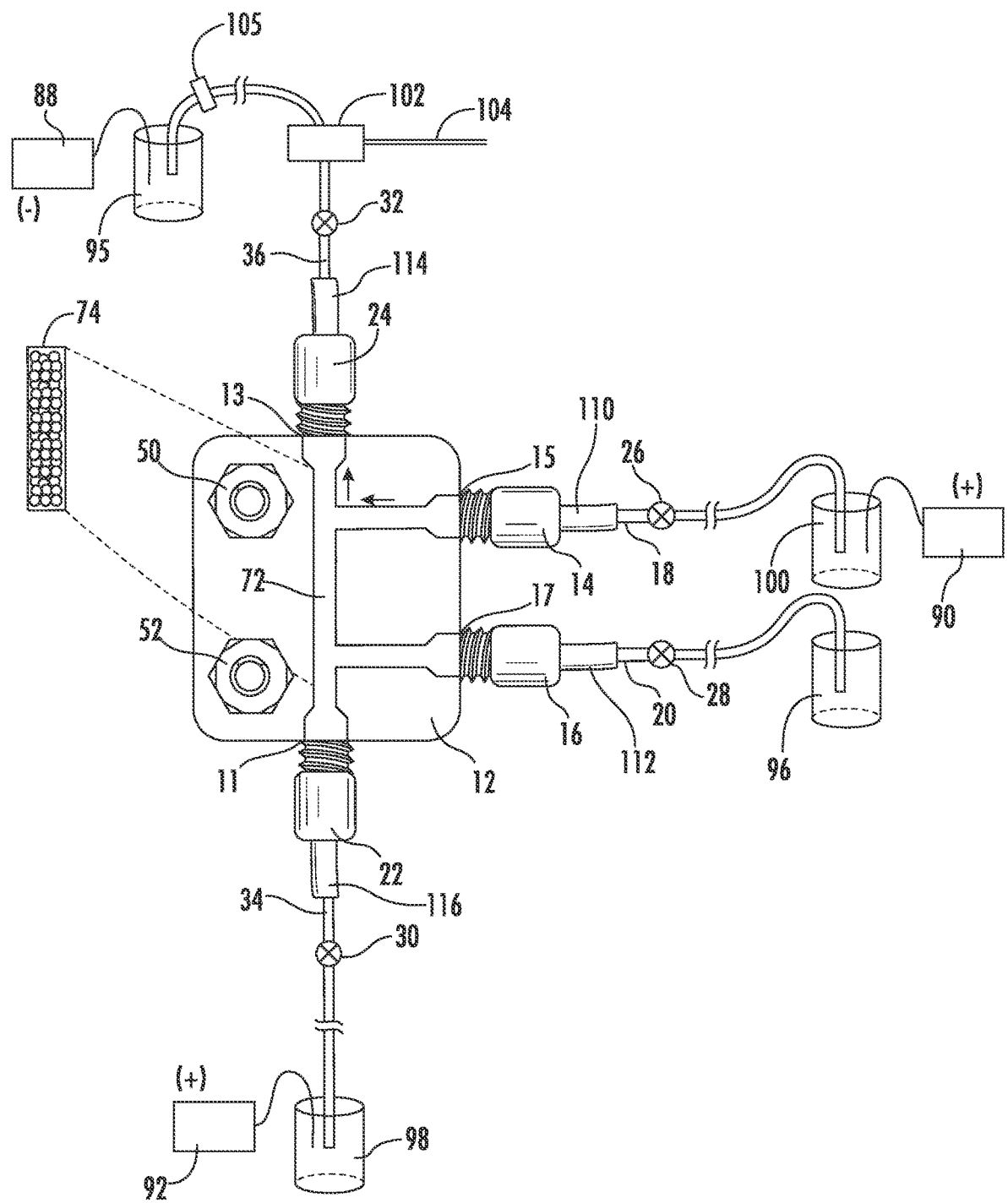

Under certain circumstances, the separation buffer may affect the integrity of the immobilized affinity ligands. For this reason, an alternative protocol was developed to provide a system where optimal binding and optimal separation can occur. For example, the use of certain acidic buffers such as formic acid, which usually yield an intense protein-peptide signal when using mass spectrometry, can also compromise the integrity of an immobilized antibody or others affinity ligands. In this case, the following protocol was designed: After the sample containing the target analyte(s) is introduced into the ACM device, the analyte(s) captured by the immobilized antibodies, and followed by a washing procedure to remove all non-specifically bound substances, as described above, the ACM device is filled with an appropriate optimal buffer to maintain full integrity of the immobilized antibody and to maintain stable binding conditions for the antibody-analyte complex. At this stage micro-valves 28 and 30 are closed and micro-valves 26 and 32 are open as shown in FIG. 8D. Introduction of a second buffer, used as optimal separation buffer, is carried out from the inlet side of transport capillary or passage 18 through analyte concentrator-microreactor (ACM) device 12, away from matrix 74 and toward the outlet end of separation capillary or passage 36. This buffer may contain additives that will improve the selectivity of the target analyte(s) to be separated. The buffer composition can be made with simple or complex additives and be compatible with common detectors used such as ultraviolet or fluorescence, or have a different composition to be compatible with mass spectrometry.

Figure 8E:
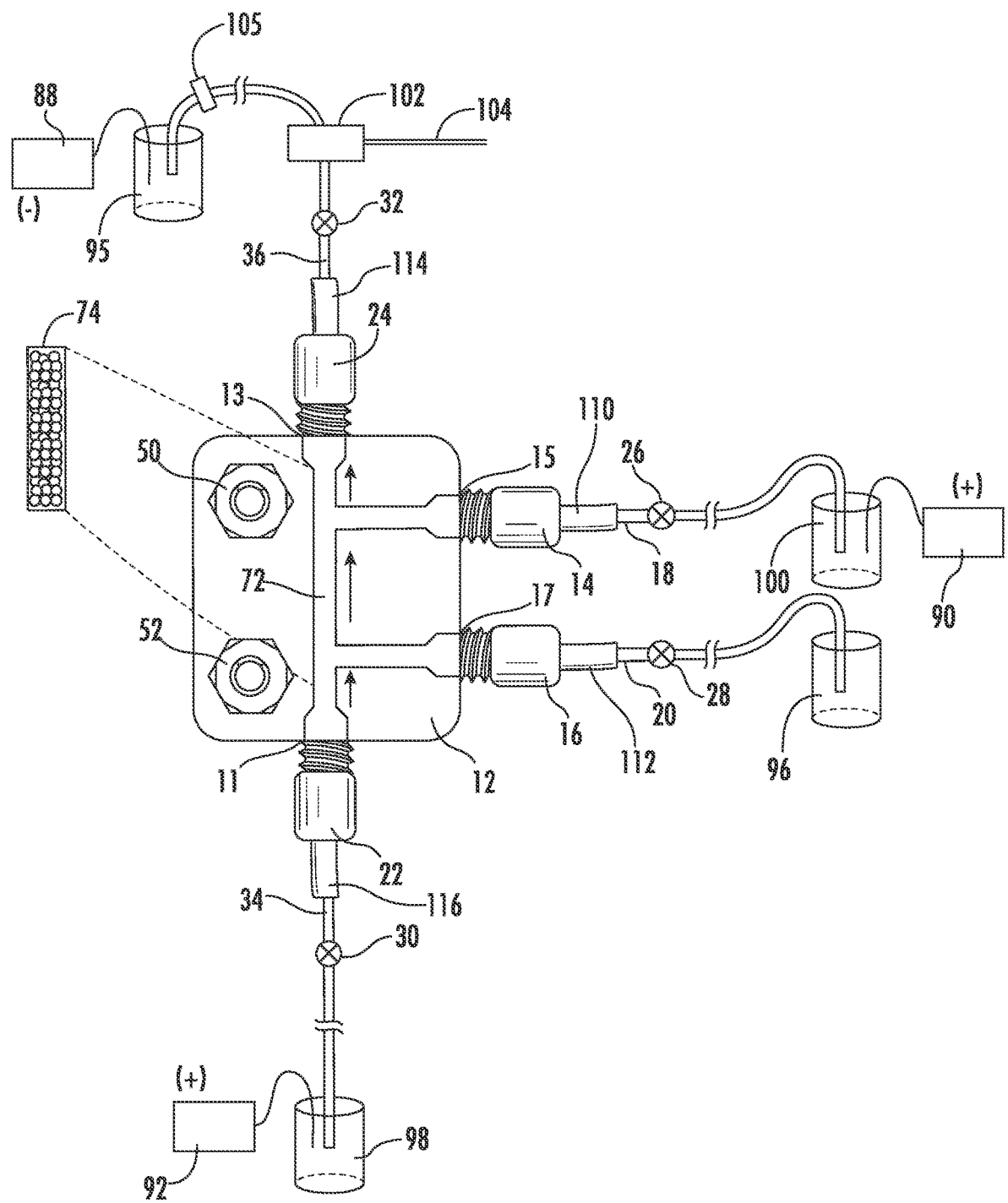

Once the second buffer is introduced completely into separation capillary or passage 36, micro-valve 26 is closed and micro-valve 30 is open, an elution process is initiated from the inlet side of separation capillary 34 as shown in FIG. 8E. A plug of buffer or solution is introduced into separation capillary or passage 34 followed by a buffer in container 98 that can preserve the integrity of the immobilized antibodies or other affinity ligands immobilized to solid-support matrix 74. Electro-osmotic flow, mechanical pressure, and/or a combination of electro-osmotic flow and mechanical pressure can usually carry out the introduction of the plug and buffer. High-voltage power supply 92 connected by an electrode, composed of a platinum-iridium wire, to container 98 is activated, having the grounding electrode connected from container 95 to a grounding platform or system.

Figure 8F:
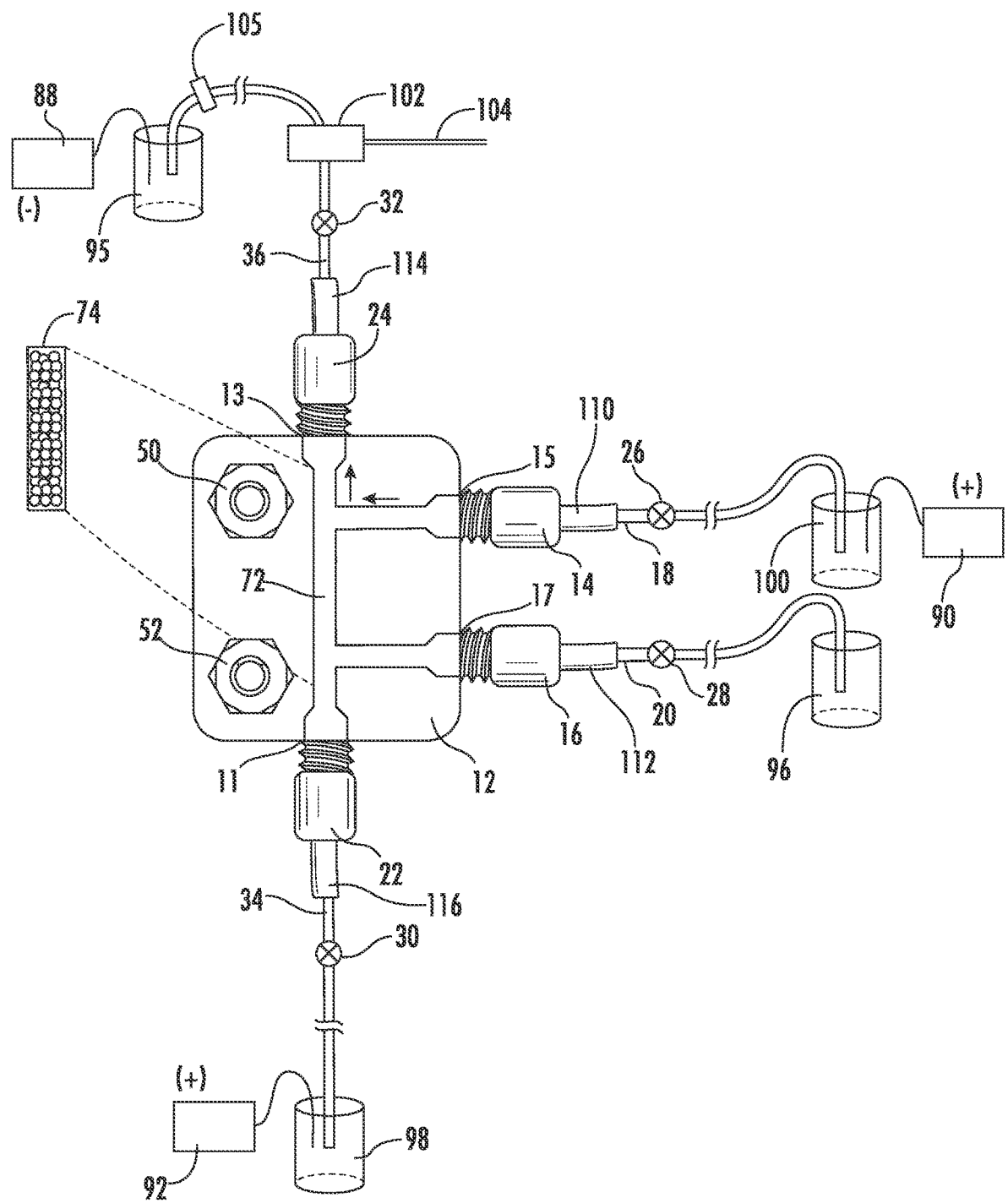

After the plug passed through matrix 74 and release all bound analytes from the immobilized antibodies, detector 102, which is connected to a photomultiplier and a computer system (not shown), via fiber optic 104 will signal that all analytes are out of analyte concentrator-microreactor (ACM) device 12. At this stage, the high-voltage power supply 92 is de-activated, micro-valve 30 is closed, micro-valve 26 is open, and high-voltage power supply 90, connected to container 100, and containing the appropriate separation buffer is activated as shown in FIG. 8F. For example, high-voltage power supply 90 can apply a voltage in the range of about 2,000 volts to 30,000 volts, and an electrical current in the range of about 10 microamperes to 200 microamperes. An appropriate cooling-heating temperature control system is recommended can be used to maintain a fixed temperature to yield consistent and reproducible results. Uncontrolled temperatures distort the separation and may denature the biomolecules under analysis. Electrical charge, electro-osmotic flow, mechanical pressure, and/or a combination of electro-osmotic flow and mechanical pressure can be used for the separation of the target analytes. The election of the appropriate method to separate the analytes is based on the composition of the separation buffer. For example, it can be a simple buffer or a buffer containing one or more additives. It can also be composed of a gel structure where only electrical charge can be used.

Another useful application that benefits by the design of the two buffers configuration is the simultaneous on-line preconcentration coupled with capillary isoelectric focusing and/or transient isotachophoresis. The use of carrier ampholites, after the immobilized antibodies (and/or other affinity ligands) have captured the target analyte(s), should be introduced throughout transport capillary or passage 18. Similarly, the anode and cathode solutions required for the capillary isoelectric focusing experiments should also be introduced using transport capillary or passage 18. Similarly, capillary transient capillary isotachophoresis, which requires a leading electrolyte and a terminating electrolyte, should be introduced using transport capillary or passage 18. Once the appropriate buffers and solutions are introduced into separation capillary or passage 36, and the bound analyte(s) is releases from matrix 74, then the respective micro-valves are closed or open, and the separation can be carried out using the separation buffer in container 100 and high-voltage power supply 90.

Under these conditions, the integrity of the immobilized antibodies in matrix 74 can be preserved and repetitively the antibodies can be used multiple times making the technology of immunoaffinity capillary electrophoresis a cost effective technique, and also capable of yielding reproducible assays when using internal calibrator standards.

Connectors 14, 16, 22 and 24 tightly attached to analyte concentrator-microreactor (ACM) device 12 by screw threads 11, 13, 15 and 17 and tubing 110, 112, 114 and 116 are also capable of accommodating respectively transport capillaries or passages 18 and 20 and separation capillaries or passages 34 and 36 with the purpose of fitting capillaries with different internal and external diameters can be used for different instrument designs and for optimal separation conditions. Tubing 110, 112, 114 and 116 can be made of plastic.

Figure 9A:
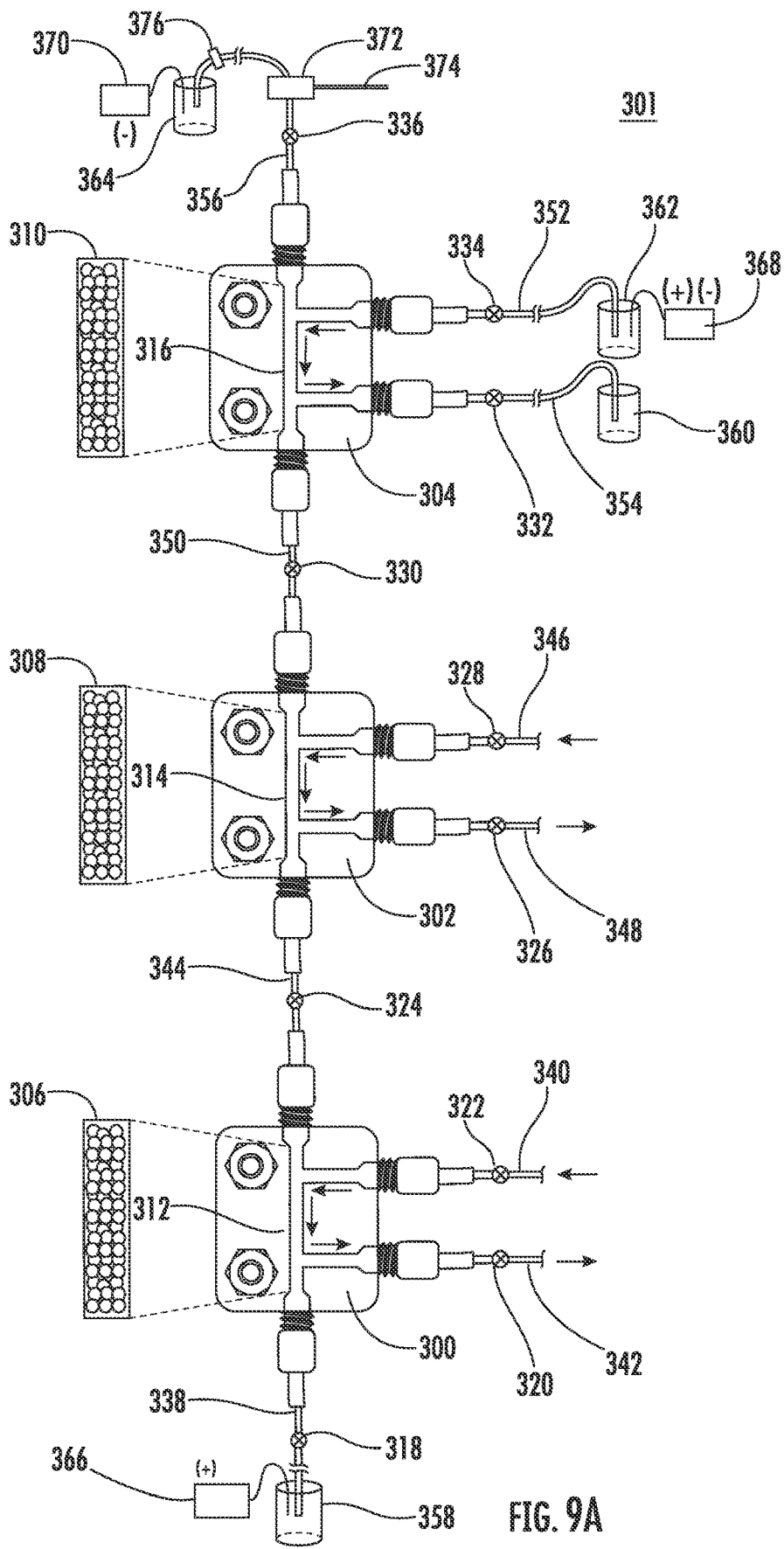
FIGS. 9A-9F are perspective views of a method of using the T-shaped support containing three an analyte concentrator-microreactors.

FIGS. 9A-9F illustrate an additional protocol to be used with three analyte concentrator-microreactor (ACM) devices 300, 302, and 304 as shown in FIG. 9A. The purpose of this protocol is to provide a design by which each analyte concentrator-microreactor ACM device 300, 302 and 304 has a different and separate function. Each analyte concentrator-microreactor ACM device 300, 302 and 304 can operate using the same separation buffer and a single high-voltage power supply as described in FIG. 7, or can operate with two or more buffer systems, as described in FIG. 8, and with an additional high-voltage power supply.

A major application of system 301, comprising three analyte concentrator-microreactor ACM devices 300, 302 and 304, is for the quantification and characterization of selective peptide biomarkers generated from isolated complex proteins. Also, it can be applied to the quantification and characterization of small molecular units derived from various other types of biopolymers. The first protocol or method for the operation of system 301 comprises using the first of the three analyte concentrator-microreactor ACM devices as a selective on-line preconcentrator unit. This first protocol starts with the immobilization of one or more distinct affinity ligands to the surface of each of solid-support matrices 306, 308, 310 prior to be deposited into cavities 312, 314, and 316 of ACM devices 300, 302, and 304, independently and separately. Elongated cavities 312, 314, and 316 can be an elongated tubular portion or channel. Conventional protocols described in the literature can be used to immobilize proteins to various types of surfaces (Kim D, Herr A E, Biomicrofluidics, volume 7, 041501, 2013; doi: 10.1063/1.4816934). Each of solid-support matrices 306, 308, 310 can be positioned in their respective elongated cavities 312, 314, and 316 with the use of frits if the solid support is composed of non-magnetic beads. Alternatively, if the solid support is composed of beads containing some metallic elements, then solid-support matrices 306, 308, 310 can be positioned in their respective elongated cavities 312, 314, and 316 with the use of one or more fixed magnets, or with the use of a magnet in motion using a mechanical system for rotation of the magnetic beads. The fixed or rotating magnets are to be positioned in the external sidewall of the ACM device. Other alternatives to be used without the presence of frits is, for example, a matrix made of a continuous block of porous structures or monoliths, or a matrix held in place by the use of restrictions points, or by interconnecting the beaded microstructures to each other and/or to the surface of the wall of the inner cavity or channel of the ACM device.

The general protocol or method for the operation of system 301 is identical to the one described in FIGS. 6, 7 and 8 for one ACM device. However, the process of operation for system 301 is different.

Figure 9B:
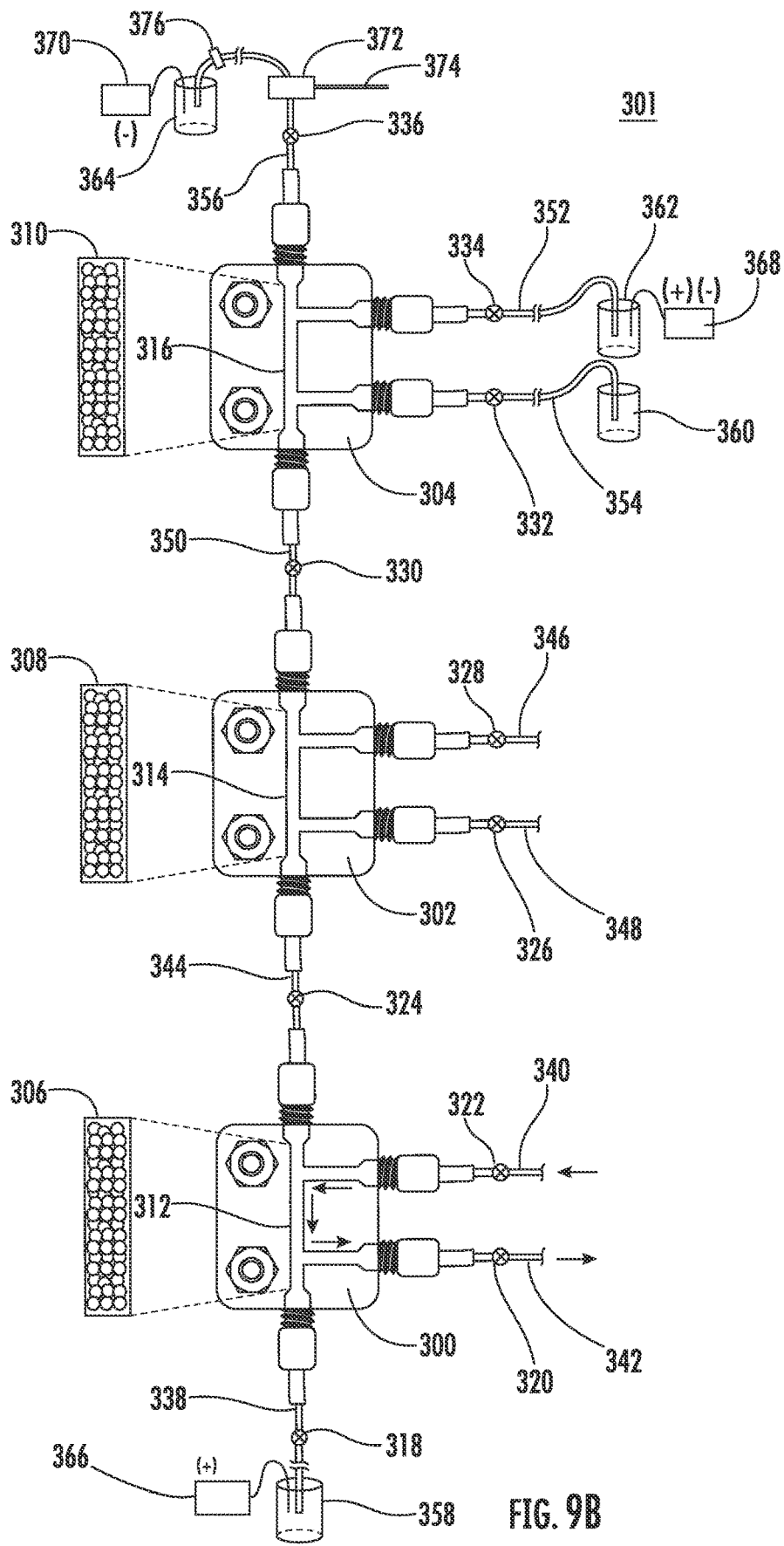

In this first protocol, matrix 306 is positioned in cavity 312 of three analyte concentrator-microreactor (ACM) device 300 and the path of fluid circulating through the matrix is controlled by micro-valves. Micro-valves 318, 324, 326, 328, 330, 332, 334, and 336 are closed and micro-valves 320 and 322 are open as shown in FIG. 9B. At this stage, a washing buffer or solution (without compromising the integrity of the immobilized affinity ligands) to remove all loosely-bound materials is introduced from the inlet side of transport capillary or passage 340, passing elongated cavity 312 of analyte concentrator-microreactor (ACM) device 300, containing matrix 306 with immobilized antibodies and/or other affinity ligands, all the way through the outlet side of transport capillary or passage 342. After the washing buffer introduction is completed, a conditioning buffer aimed to maximize the binding process is passed through the same path, followed by the sample under study (a biological fluid or cell-tissue extract)

The sample under study can contain preferentially only one target proteoform, or it can have two or more proteoforms, if the target proteoforms are associated with the same disease. The purpose of this strategy is to obtain either one single peptide biomarker identifying the disease or more than one biomarker, or a panel of peptide biomarkers, that may provide additional information about the disease, such as for example, to provide a highly accurately diagnosis, to provide a prognosis of the disease as well, and to further monitor any molecular changes during therapy.

After the sample has been introduced into analyte concentrator-microreactor (ACM) device 300, allowing the target proteoform(s) to bind non-covalently to the immobilized affinity ligand, a cleaning buffer is applied to remove all excess amount of sample and unwanted substances bound non-specifically to surfaces, and without compromising the binding of the isoform(s) to the immobilized affinity ligands. The washing buffer, the sample, and the cleaning buffer or solution, are introduced preferentially by mechanical pressure, from the inlet side of transport capillary or passage 340, all the way to the outlet side of transport capillary or passage 342. Other introduction methods can be used, such as electromigration, electro-osmotic flow, or a combination of mechanical pressure and electro-osmotic flow. All containers utilized in the experimental protocol for providing sample and buffers or solutions can be interchangeably and used separately for each individual sample and buffers or solutions.

Figure 9C:
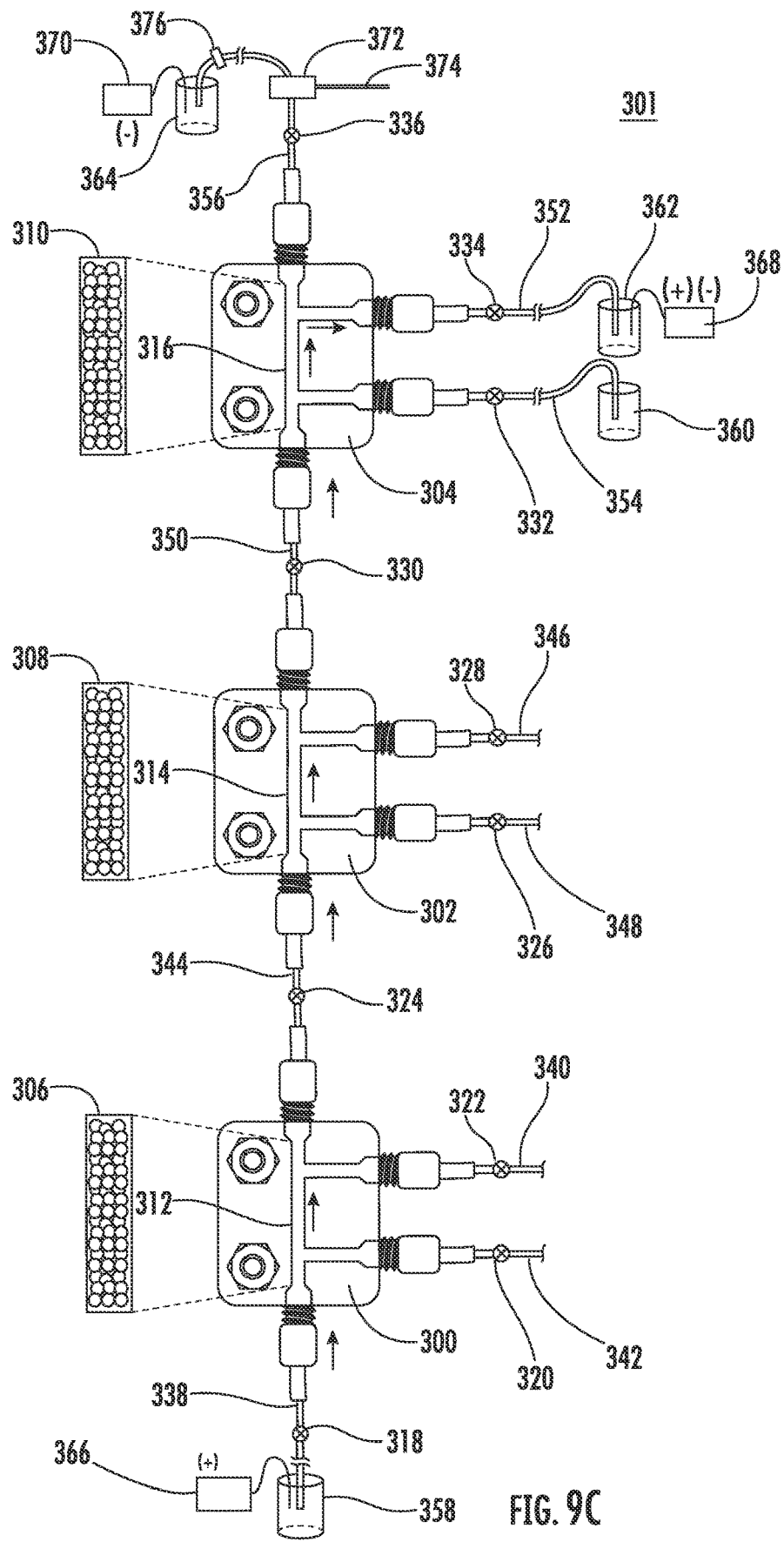

Once the excess amount of sample and unwanted substances are removed from the system, a process of elution or release of the bound analyte(s) from matrix 312 starts. Prior to this process, micro-valves 320 and 322, 326, 328, 330, 332, and 336 are closed, and micro-valve 318, 324, 330, and 334 are open as shown in FIG. 9C. A second method or protocol is carried out.

The second protocol or method for the operation of the three ACM devices system consists of using the second of the three ACM devices, which is analyte concentrator-microreactor (ACM) device 302 as an on-line microreactor unit. This second protocol starts with an optimization condition for one or more distinct proteolytic enzymes previously immobilized to matrix 308 positioned in elongated cavity 314 of analyte concentrator-microreactor (ACM) device 302. A suitable immobilization protocol is basically the same as those standard chemical methods used for the immobilization of the one or more affinity ligands described in the literature (Kim D, Herr A E, Biomicrofluidics, volume 7, 041501, 2013; doi: 10.1063/1.4816934; Datta S, Christena L R, Rajaram Y R S, 3 Biotech, Volume 3, pages 1-9, 2012; doi: 10.1007/s13205-012-0071-7). The immobilization is through a direct chemistry to the solid support, using a spacer arm, or immobilized through a previously immobilized molecular entity. Immobilization of enzymes onto solid supports provides an effective means of enhancing enzyme catalytic properties and in many cases improving enzyme stability.

Prior to the release of the bound proteoform(s) from matrix 306, an optimization buffer is introduced from the inlet side of capillary or passage 318, all the way through separation capillary or passage 338, matrix 306 of analyte concentrator-microreactor (ACM) device 300; separation capillary 344, matrix 308 of analyte concentrator-microreactor (ACM) device 302; separation capillary or passage 350, and matrix 310 of analyte concentrator-microreactor (ACM) device 304, to exit through capillary or passage 352 to waste container 362.

After the optimization buffer is introduced into capillary or passage 318 and exiting through capillary or passage 352, a plug of an elution buffer followed by a separation buffer is introduced from the inlet side of capillary or passage 310 using primarily mechanical pressure. Alternatively, electro-osmotic flow, or a combination of electro-osmotic flow and mechanical pressure can be also used. For this to occur, high-voltage power supply 366 is activated, and power supply 368 can act as a grounding system, in this special case. High-voltage power supply 368 can alternatively act as a high-voltage positive side, as it is described in the next protocol (a third protocol). As the elution plug releases the bound proteoform(s) from matrix 306 of analyte concentrator-microreactor (ACM) device 300, and the protein form(s) enter in contact with the immobilized proteolytic enzymes in matrix 308 of analyte concentrator-microreactor ACM device 302, where peptides are formed. After the peptides exit analyte concentrator-microreactor (ACM) device 302, they continue the path to enter into matrix 310 of analyte concentrator-microreactor (ACM) device 304.

The affinity ligands immobilized to matrix 310 of analyte concentrator-microreactor (ACM) device 304, can be a molecular entity formed by a single type of affinity ligands, such as antibodies, antibody fragments, nanobodies, lectins, aptamers, or they can be molecular entities of other types of affinity ligands or forms by a combination of them. Many proteoforms can be glycoproteins and, therefore, one or more of generated peptides can be glycopeptides. Additionally, there may also be present peptides with one or more type of molecular modifications, such as phosphorylation, hydroxylation, or others. The advantage of this technique is that it will be possible to identify potential peptide biomarkers with unique modifications that will be able to differentiate, for example, between aggressive type of tumors, indolent types, and benign types. A typical example is prostate cancer, in which the natural course of the cancer is variable and it is difficult to determine prognosis on the basis of clinical information (See, Culig Z, Recent Results in Cancer Research, volume 202, pages 141-147, 2014; doi: 10.1007/978-3-642-4519-9_17, Lu G, Crihfield C L, Gattu S, Veltri L M, Holland L A, Chemical Reviews in press, 2018; doi: 10.1021/acs.chemrev.7b00669).

The cleavage of a protein, or protein digestion, by one or more proteolytic enzymes is a crucial step to obtain peptides and a key procedure for the characterization of proteins, for example by mass spectrometry. The proteolytic process can be simple or complex, depending on the complexity of the protein. Conventional off-line proteolysis made in solution need lower amounts of proteases, in comparison to the amount of the protein to be digested. A low weight ratio (typically 1:20 to 1:100) between protease and protein is usually employed, requiring incubation times of 12 or more hours at 37 degree Celsius. Using immobilized enzymes permits the use of larger amounts of proteolytic enzymes as much as a weight ratio of 1:1. This protocol make the enzyme(s) more stable, less likely to denature, and block the possibility of self-digestion that can happens when using proteolytic enzymes in solution. Another important feature of an immobilized enzyme is that the cleavage is quite consistent, under the same experimental conditions, it can be re-used multiple times and the cleavage is accomplished in a short period of times, usually within minutes. The process of cleavage can be accelerated by the use of ultrasonic waves, named microwave-assisted proteolysis, infrared radiation, organic and detergent-assisted methods, power ultrasound with elevated pressure and temperature, or by alternating current.

Furthermore, when using complex proteins containing disulfide bridges it is required to denature the protein molecule first, usually with high concentration of a chaotropic denaturant such as urea. Under these circumstances, the protein under study undergoes a process of disruption of both its secondary and tertiary structure. The process of denaturation is followed by reduction of the protein. Reducing agents, such as dithiothreitol, tributylphosphine, tris(2-carboxyethyl)phosphine, sodium borohydrate, sodium phosphorothioate, or mercaptoethanol, disrupt the disulfide bonds. After denaturation and reduction of complex proteins, a process of alkylation or "capping" of reduced cysteine residues is commonly performed by an alkylating agent such as iodoacetamide. This process prevents proteins from aggregating and precipitating due to oxidative cross-linking.

Figure 9D:
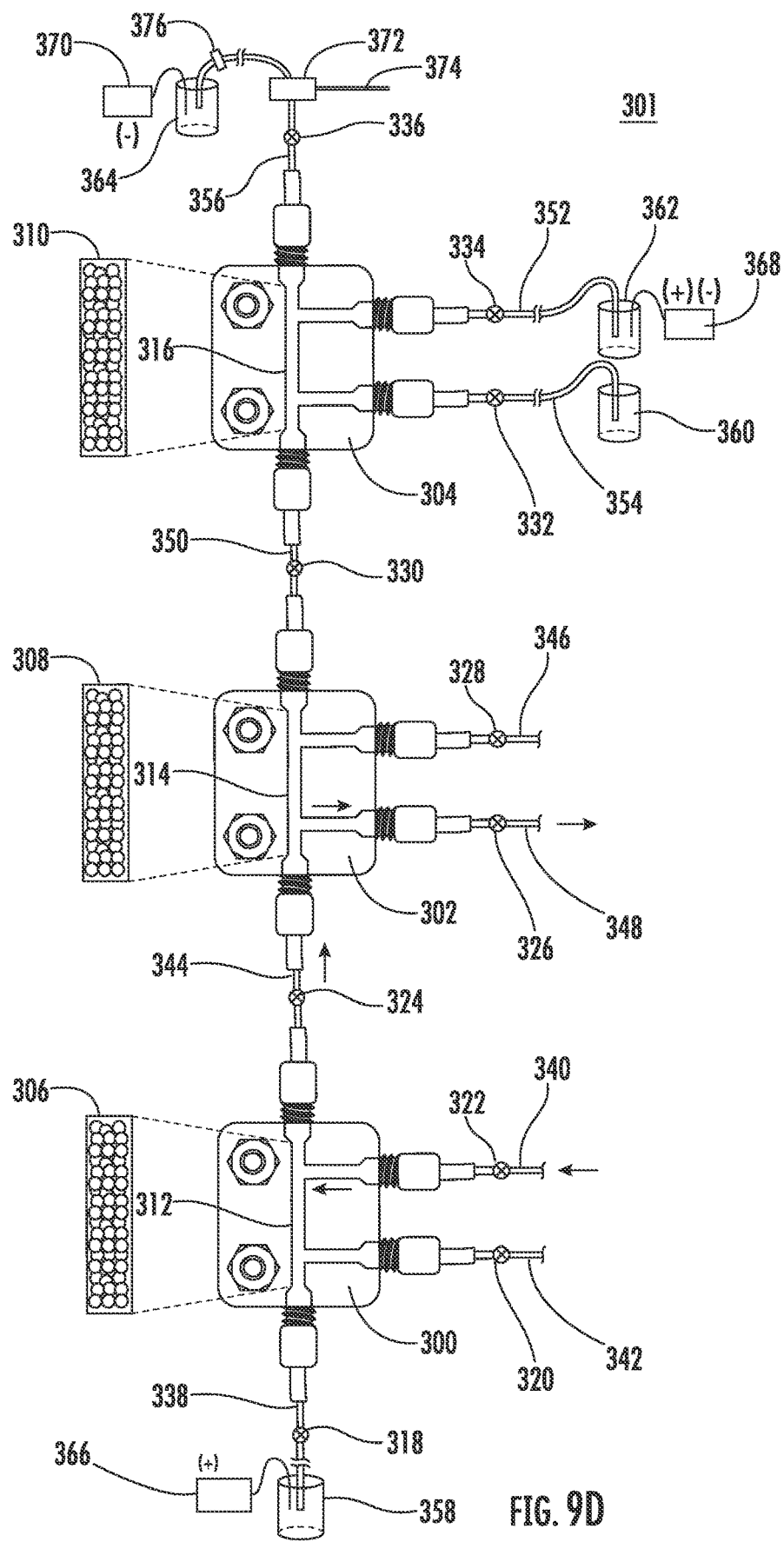

With the procedure described here an improved protein digestion can be implemented. Micro-valves 322, 324 and 326 are open and all other micro-valves are closed as shown in FIG. 9D. A denaturing-reduction-alkylation buffer or solution can be introduced from the inlet side of capillary or passage 340, through separation capillary or passage 344, and exiting on the outlet side of capillary or passage 348. This buffer will not be in contact with matrix 306 of analyte concentrator-microreactor (ACM) device 300, or matrix 308 of analyte concentrator-microreactor (ACM) device 302. At this stage, micro-valves 320, 322, 326, 328, 332 and 336 are closed as shown in FIG. 9C. Micro-valves 318, 324, 330 and 334 are open. An elution process to release the proteoform(s) is carried out as described above. It should be emphasized here that the denaturing-reduction-alkylation buffer protocol, used in the portion of the separation capillary or passage 344, is not used in the protocol described above in this section. The process of protein digestion by immobilized proteolytic enzymes to be carried out in analyte concentrator-microreactor (ACM) device 302 can be implemented by ultrasonic waves, infrared radiation, alternating current, or other methods. The use of multiple immobilized enzymes and a longer elongated cavity 314 of analyte concentrator-microreactor (ACM) device 302 can be effective in obtaining some crucial biomarker peptides, with just the use of a denaturing agent, but without the need for reduction or alkylation of the protein.

A uniform controlled temperature system can be designed for all three ACM devices and their respective connected separation capillaries, or it can be designed as modular units controlled independently and separately.

Once the excess amount of on-line generated peptides not bound to matrix 310 exits capillary or passage 352, a cleaning buffer is introduced from the inlet of capillary or passage 318 to the outlet of capillary or passage 352. This buffer is aimed to remove all unwanted materials bound to the separation and transport capillaries.

At this stage, a third method or protocol is carried out.

The third protocol or method for the operation of system 301 comprises using the third of the three ACM devices which is analyte concentrator-microreactor (ACM) device 3024 as a selective on-line preconcentrator unit. This third protocol starts with the optimization conditions for the one or more distinct affinity ligands previously immobilized on the matrix 310 positioned in cavity 316 of analyte concentrator-microreactor (ACM) device 304.

The desired peptides, glycopeptides, or peptides containing other co-translational or post-translational modified amino acid residues are now captured by one or more affinity ligands immobilized to matrix 310, positioned in cavity 316 of analyte concentrator-microreactor (ACM) device 304.

The option to immobilize multi-affinity ligands, aimed to capture different types of modified and/or non-modified peptides, is of significant advantage due to the fact that it will capture more selective peptides that can be used as specific biomarkers of wellness or disease. The use of system 301 with the three ACM devices protocol can be applied to one or more isolated proteins derived from biological fluids or extracts of biological fluids, or to peptides derived from an entire biological fluid, which is known as "peptidomics". Peptidomics is defined as the comprehensive qualitative and quantitative analysis of all peptides in a biological sample (See, Dallas D C, Guerrero A, Parker E A, Robinson R C, Gan J, German J B, Bartle D, Lebrilla C B, Proteomics, volume 15, pages 1026-1038, 2015; doi: 10.1002/pmic.201400310).

After removing all unwanted materials by a cleaning buffer, a separation buffer is introduced from the inlet side of separation capillary or passage 338, or in a more convenient way, from the inlet side of separation capillary or passage 354.

Figure 9E:
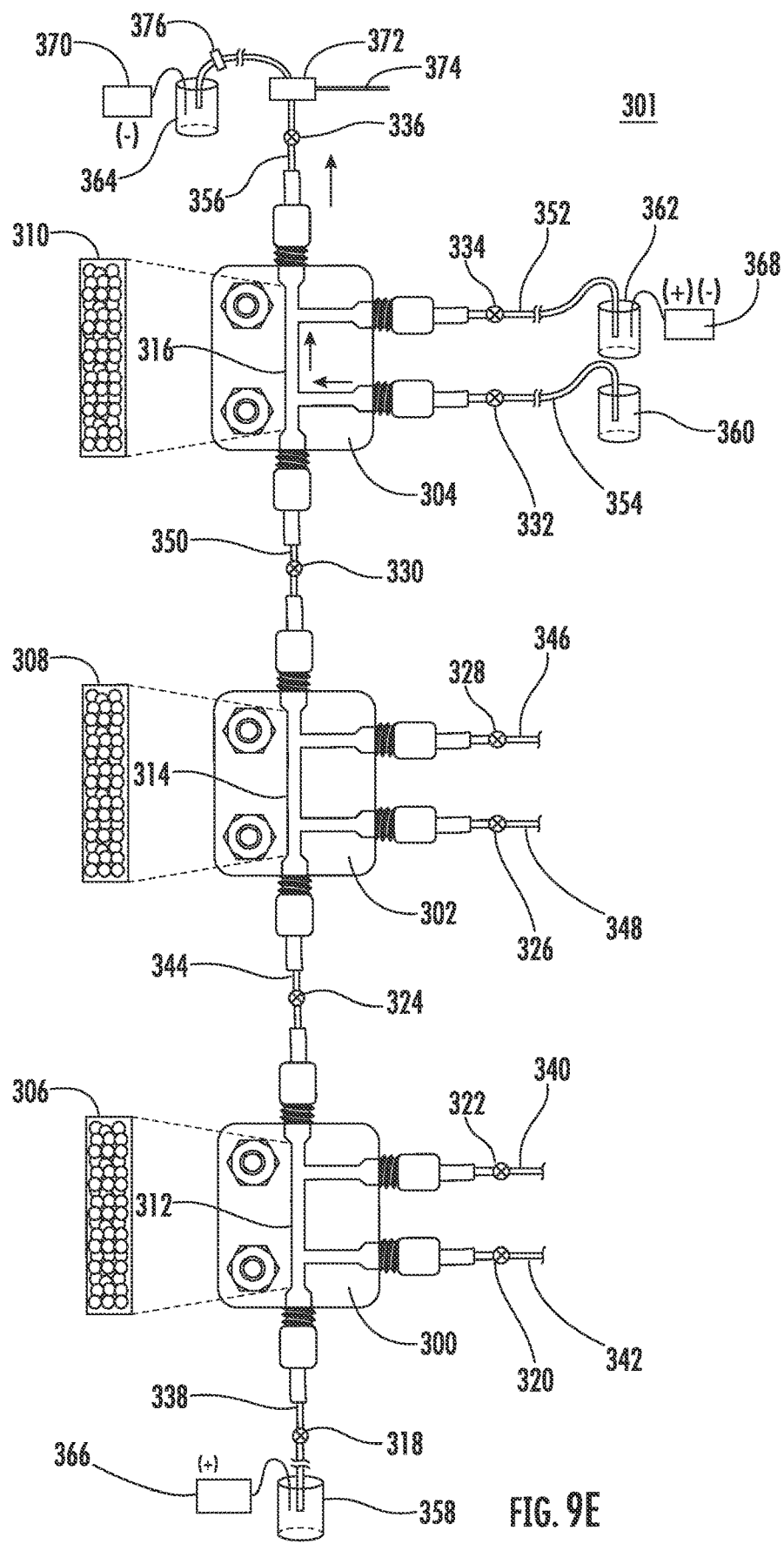

If the introduction of a small volume or plug of an elution buffer to release the bound peptides to matrix 310 is to be made from the inlet side of capillary or passage 354, then micro-valves 332, and 336 are open. Micro-valves 318, 320, 322, 324, 326, 328, 330, 334 are closed as shown in FIG. 9E. The introduction of a plug of an elution buffer, followed by a separation buffer can be carried out preferentially at a low amount of mechanical pressure (expressed as pound-force per square inch or psi). Alternatively, the introduction of a plug of an elution buffer can be performed by electromigration, electro-osmotic flow, or a combination of electroosmotic flow and mechanical pressure. For this, another high-voltage power supply (not shown) must be connected, by using a high-voltage cable and platinum-iridium wire, to container 360. This additional power supply (not shown) must be activated if need to be used.

Figure 9F:
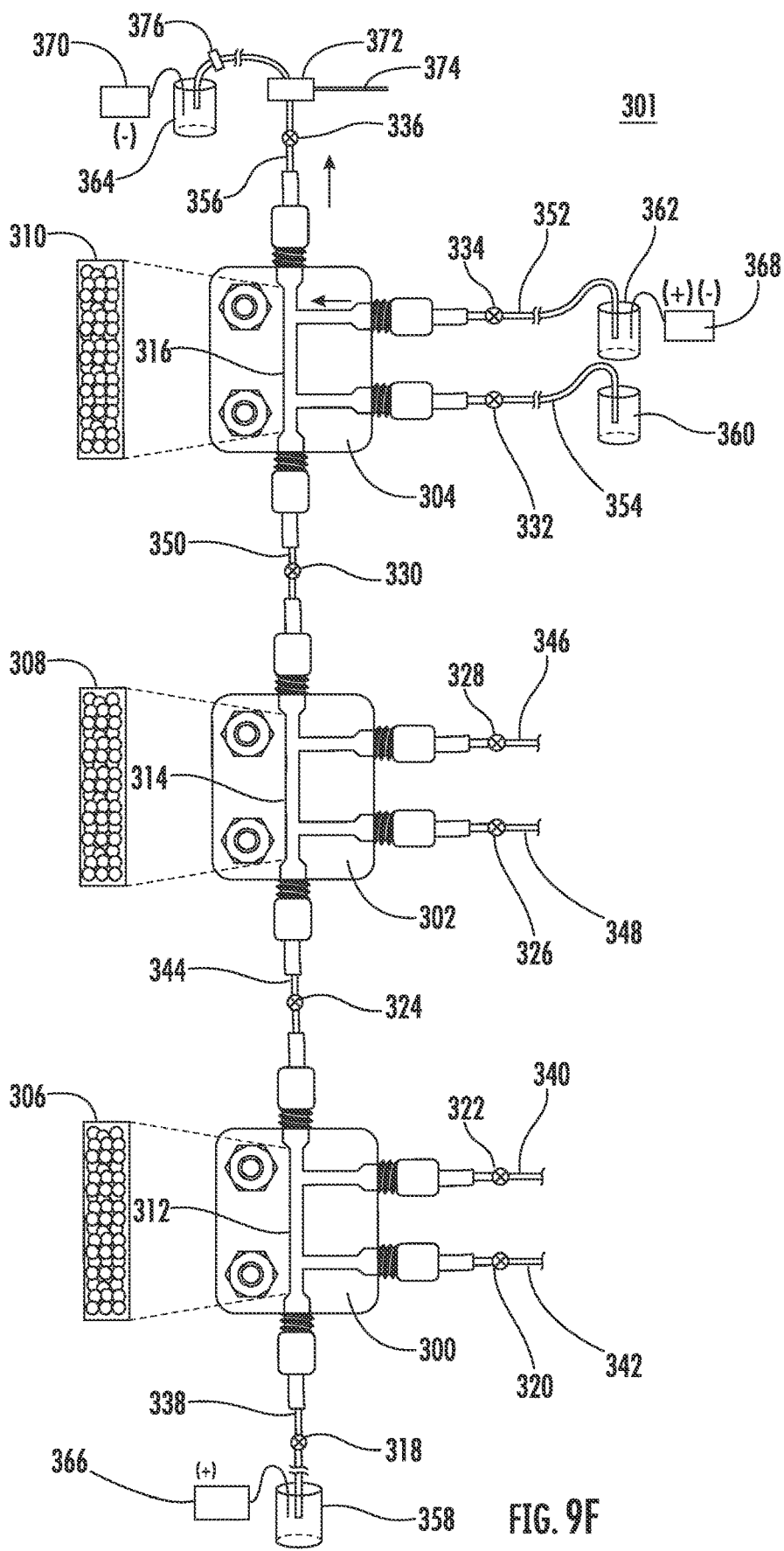

The passing of the plug of an elution buffer, or solution, from the inlet side of separation capillary or passage 354, passing through matrix 310 containing the bound peptides, will release the bound peptides out of analyte concentrator-microreactor (ACM) device 304 into separation capillary or passage 356. High-voltage power supply 368, with positive polarity, connected to container 362 by a platinum-iridium wire, and high-voltage power supply 370, with negative polarity, connected to container 364 by a platinum-iridium wire (grounding side), are activated. As soon as the released peptides passed through and are monitored by an on-line detector 372, the motion of fluid is stopped. Monitor 372 is connected through fiber optic 374 to a detection-monitor system located outside the T-shaped support system (not shown). At this stage micro-valve 332 is closed and micro-valve 334 is open as shown in FIG. 9F. Micro-valve 336 continues open and all other micro-valves continue closed. Container or vessel 362 contains an optimal separation buffer to best separate the target peptides. This involves the use of one or more of the various modes of capillary electrophoresis. It can also be combined with transient isotachophoresis; implementation of the separation buffer chemical additives such as detergents, organic solvents, urea, or other substances, individually or in combination. If the outlet end of separation capillary or passage 356 is connected to a mass spectrometer or another detector, which require special buffer, then a compatible buffer with the detector is to be used. For other detection means, such as ultraviolet, fluorescence or laser-induced fluorescence, detector 376 is used. Additional detection systems, such as nuclear magnetic resonance, circular dichroism, conductivity and others can also be used individually or in combination with other detector systems.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. An integrated modular unit, comprising:
   a support box;
   a modular analyte concentrator-microreactor (ACM) device attached to the support box;
   the analyte concentrator-microreactor (ACM) device having a first port, a second port, and a third port, a three way junction comprising an elongated first channel between the first port and the third port and a second channel having a first end connected to the first channel, the second port at a second end of the second channel, the elongated first channel being perpendicular to the second channel;
   a first separation capillary having a first end connected to the first port of the analyte concentrator-microreactor (ACM) device;
   a second separation capillary having a first end connected to the third port of the analyte concentrator-microreactor (ACM) device;
   a first transport capillary having a first end connected to the second port of the analyte concentrator-microreactor (ACM) device, and
   a connector-support structure formed of a first arm, a second arm and a third arm converging at a connection-separation point, the first arm being perpendicular to the second arm and the third arm, a second end of the first separation capillary and a second end of second separation capillary being received in the first arm of the connector-support structure to converge the first separation capillary and the second separation capillary to the connection separation point within the connector-support structure, the second end of the first separation capillary extending through the second arm of the connector-support structure and the second end of the second separation capillary extending through the third arm of the shaped connector-support structure.

2. The integrated modular unit of claim 1 wherein the elongated first channel of the analyte concentrator-microreactor (ACM) device comprising a plurality of microstructures therein.

3. The integrated modular unit of claim 2 wherein one or more affinity ligands are immobilized to the plurality of microstructures within the elongated first channel of the analyte concentrator-microreactor (ACM) device.

4. The integrated modular unit of claim 1 further comprising;
   a detection system coupled to the second end of the second separation capillary.

5. The integrated modular unit of claim 4 wherein the detection system is one or more detectors selected from ultraviolet, fluorescence, laser-induced fluorescence, mass spectrometer, nuclear magnetic resonance, circular dichroism, electrochemical, conductivity, charged coupled device (CCD), chemiluminescence, bioluminescence radioactive, and modified versions of these detectors.

6. The integrated modular unit of claim 3 wherein the one or more affinity ligands immobilized to the plurality of microstructures are immobilized by physicochemical interactions or by covalent chemical interactions.

7. The integrated modular unit of claim 1 further comprising:
   controlling means for independently controlling flow in the first separation capillary through the analyte concentrator-microreactor (ACM) device using electromigration, electro-osmotic flow, mechanical pressure or a combination of electro-osmotic flow and mechanical pressure to a second end of the first transport capillary, and for separately and independently controlling flow through the first separation capillary and through the analyte concentrator-microreactor (ACM) device using electromigration, electro-osmotic flow, mechanical pressure or a combination of electro-osmotic flow and mechanical pressure to the second end of the second separation capillary.

8. The integrated modular unit of claim 7 wherein the controlling means comprises a micro-valve system, the micro-valve system having a first valve in the second separation capillary and a second valve in the first transport capillary and a computer-control system, the computer-control system controlling closing and opening of the first valve and the second valve.

9. The integrated modular unit of claim 1 wherein the first separation capillary is connected to the first port with a first connector, the second separation capillary is connected to the third port with a second connector and the first transport capillary is connected to the second port with a third connector.

10. The integrated modular unit of claim 1 wherein the analyte concentrator-microreactor (ACM) device is mounted to the support box with one or more screws.

11. The integrated modular unit of claim 1 further comprising a cartridge-cassette, the second end of the first separation capillary and the second end of the second separation capillary being connected to the cartridge-cassette.

12. The integrated modular unit of claim 11 wherein the support box is attached to the cartridge-cassette with one or more screws.

13. The integrated modular unit of claim 12 wherein the analyte concentrator (ACM) device and the cartridge-cassette are manufactured as a single integrated modular unit.

14. The integrated modular unit of claim 11 further comprising a tube wherein the second arm of the connector-support structure and the third arm of the connector-support structure are coupled to the cartridge-cassette with the tube, said second end of the second separation capillary and said second end of the first separation capillary being within the tube.

15. The integrated modular unit of claim 14 wherein the tube comprises a cooling or heating within the tube.

16. The integrated modular unit of claim 14 further comprising tubing connected to the first arm of the connector-support structure, a sealing material in the tubing sealing the first separation capillary and the second separation capillary to the connection-separation point.

17. The integrated modular unit of claim 1 further comprising a second one of the analyte concentrator-microreactor (ACM) device connected to and between the second separation capillary and the connector-support structure, the first elongated channel of the second analyte concentrator-microreactor (ACM) device comprising second microstructures therein, the second microstructures comprising beads.

18. The integrated modular unit of claim 17 wherein the beads are made from glass, plastic, sol-gels, monolithic polymers, polymeric materials, ceramic, or metallic compositions, and mixtures thereof.

19. The integrated modular unit of claim 1 further comprising microstructure bound to an internal wall of the second separation capillary.

20. The integrated modular unit of claim 1 wherein a portion of the first transport capillary connected to the second port of the analyte concentrator-microreactor (ACM) device has a bore internal diameter in a range of about 50 micrometers to about 200 micrometers and a portion of the second separation capillary connected to the third port of the analyte concentrator-microreactor (ACM) device has a bore internal diameter in a range of about 5 micrometers to about 150 micrometers.

21. The integrated modular unit of claim 1 wherein the analyte concentrator-microreactor (ACM) device further comprising a fourth port, a third channel having a first end connected to the first channel, the fourth port at a second end of the third channel and further comprising a second transport capillary having a first end connected to the fourth port of the analyte concentrator-microreactor (ACM) device, the elongated first channel being perpendicular to the third channel.

* * * * *